United States Patent
Grof et al.

(10) Patent No.: US 10,607,049 B2
(45) Date of Patent: Mar. 31, 2020

(54) METHOD AND A SYSTEM FOR XRF MARKING AND READING XRF MARKS OF ELECTRONIC SYSTEMS

(71) Applicants: SOREQ NUCLEAR RESEARCH CENTER, Yavne (IL); SECURITY MATTERS LTD., D.N. Hevel Eilot (IL)

(72) Inventors: Yair Grof, Rehovot (IL); Tzemah Kislev, Mazkeret Bathya (IL); Nadav Yoran, Tel Aviv (IL); Haggai Alon, Kibbutz Naan (IL)

(73) Assignees: SOREQ NUCLEAR RESEARCH CENTER, Yavne (IL); SECURITY MATTERS LTD., D.N. Hevel Eilot (IL)

( * ) Notice: Subject to any disclaimer, the term of this patent is extended or adjusted under 35 U.S.C. 154(b) by 0 days.

(21) Appl. No.: 16/091,222

(22) PCT Filed: Apr. 4, 2017

(86) PCT No.: PCT/IL2017/050404
§ 371 (c)(1),
(2) Date: Oct. 4, 2018

(87) PCT Pub. No.: WO2017/175219
PCT Pub. Date: Oct. 12, 2017

(65) Prior Publication Data
US 2019/0156075 A1    May 23, 2019

Related U.S. Application Data

(60) Provisional application No. 62/317,859, filed on Apr. 4, 2016.

(51) Int. Cl.
*G06K 7/10* (2006.01)
*G01N 23/223* (2006.01)
(Continued)

(52) U.S. Cl.
CPC ......... *G06K 7/1099* (2013.01); *G01N 23/223* (2013.01); *G01N 2223/0766* (2013.01);
(Continued)

(58) Field of Classification Search
CPC ......... G01N 23/233; G01N 2223/0766; G01N 2223/303; G06K 7/1099; H01L 23/544; H01L 2223/54413; H05K 1/0266
See application file for complete search history.

(56) References Cited

U.S. PATENT DOCUMENTS 4,392,236 A * 7/1983 Sandstrom ........... G01N 23/223
119/215
7,623,621 B1 * 11/2009 Schramm, Jr. ....... G01N 23/223
378/44
(Continued)

FOREIGN PATENT DOCUMENTS

EP    1 534 051 A1    5/2005
EP    1936539 A1    6/2008
(Continued)

*Primary Examiner* — Mark R Gaworecki
(74) *Attorney, Agent, or Firm* — Browdy and Neimark, PLLC

(57) ABSTRACT

Methods and systems for verifying compatibility of components of an electronic system are disclosed. The method includes irradiating a first and second components presumably associated with the electronic system, with XRF exciting radiation, and in response thereto, detecting one or more XRF response signals indicative of first and second XRF signatures, emitted from the first and second components. Then the first and second XRF signatures are processed to determine whether they are associated with respectively a first and second XRF marking compositions on the first and second components, and the compatibility of the first and second components to the electronic system is determined/verified based on the correspondence between the first and a second XRF signatures. Electronic systems are also dis-
(Continued)

closed including at least a first and a second electronic components respectively having the first and second XRF marking compositions that enable verification of compatibility of the components.

21 Claims, 9 Drawing Sheets

(51) Int. Cl.
  *H01L 23/544* (2006.01)
  *H05K 1/02* (2006.01)
(52) U.S. Cl.
  CPC ...... *G01N 2223/303* (2013.01); *H01L 23/544* (2013.01); *H01L 2223/54413* (2013.01); *H05K 1/0266* (2013.01)

(56) References Cited

U.S. PATENT DOCUMENTS

| | | | |
|---|---|---|---|
| 9,699,640 B2 | 7/2017 | Kimura et al. | |
| 2003/0081719 A1 | 5/2003 | Ida et al. | |
| 2003/0194053 A1* | 10/2003 | Schramm | G01N 23/223 378/45 |
| 2005/0036583 A1 | 2/2005 | Chen et al. | |
| 2006/0187719 A1 | 8/2006 | Matsumoto | |
| 2007/0126437 A1 | 6/2007 | Sul | |
| 2008/0013679 A1 | 1/2008 | Nakagawa | |
| 2012/0093286 A1* | 4/2012 | Peterson | G01N 23/223 378/45 |
| 2014/0072095 A1* | 3/2014 | Feser | G01N 23/2206 378/4 |
| 2015/0078518 A1 | 3/2015 | Tziazas | |
| 2016/0169818 A1 | 6/2016 | Martin et al. | |
| 2018/0001565 A1* | 1/2018 | Hocker | B33Y 40/00 |

FOREIGN PATENT DOCUMENTS

| | | |
|---|---|---|
| JP | S56-54100 A | 5/1981 |
| JP | 4-320912 A1 | 11/1992 |
| JP | H05-327299 A | 12/1993 |
| JP | H07-335510 A | 12/1995 |
| JP | 2000218920 A | 8/2000 |
| JP | 2004165603 A | 6/2004 |
| JP | 2009503521 A | 1/2009 |
| JP | 2014235573 A | 12/2014 |
| WO | 89/08926 A1 | 9/1989 |
| WO | 0125821 A2 | 4/2001 |
| WO | 03/0388986 A2 | 5/2003 |
| WO | 2015/097792 A1 | 7/2015 |
| WO | 2016157185 A1 | 10/2016 |
| WO | 2017134660 A1 | 8/2017 |

\* cited by examiner

METHOD AND A SYSTEM FOR XRF MARKING AND READING XRF MARKS OF ELECTRONIC SYSTEMS

BACKGROUND AND GENERAL DESCRIPTION

The present invention is in the field of X-Ray Fluorescence (XRF) and particularly relates to XRF marking of electronic systems.

The present invention provides a novel technique for marking complementary (compatible) components of a composite system, such as an electronic system, by a unified marking/coding system/scheme (which is also referred to herein as One Board One code (OBOC) coding system/scheme.

More specifically the present invention provides for utilizing/employing elemental Id embedded in elemental (physical markings of components of electronic system) for providing brand protection and/or authentication of customized electronics, and/or providing liability of electronic components in medical devices (and in particular in wearable medical devices), and/or providing bridge liability for the coupling between virtual services or products and physical operational systems (for example the coupling between personal data and a smart clothing).

In various embodiments of the present invention the composite electronic system may be any system including an integrated circuit with plurality of components such as circuit boards (e.g. printed circuit boards (PCB) and/or flexible circuits), as well as electronic components to be electronically coupled/mounted on the circuit boards, such as processors and/or controllers and/or other chips and transistors of the circuit, data input/output/communication elements (e.g. RF and/or antenna modules), sensor modules (such as inertial sensors, camera, microphone as well as other sensors such as temperature and/or pressure and/or magnetic field sensors), user interface modules (e.g. screen, key-pad) and/or other electronic component of the composite electronic system which it to be electronically connected to the other components of the system (e.g. via the circuit board). Alternatively or additionally the composite system may be an electronic chip where one component thereof being the integrated circuit die of the chip and the second component may be the packaging of the system (of the chip) in which the die is encapsulated. Yet alternatively or additionally the composite electronic system may be for example a distributed system including one or more separate components (which may be in this case separate devices) which are configured and operable together to carry out the operation of the composite system. For instance the composite electronic system may include an electronic system (e.g. an electronic control system), such as a health monitoring/treatment controller device and a complementary smart wearable product device (smart garment) connectable to the health monitoring/treatment controller, whereby the health controller device may be adapted for monitoring a condition of a user (e.g. by utilizing suitable sensors associated/connected thereto, and the smart wearable product may be configured to be responsive to signals from the health controller device for providing treatment to the user for example by releasing certain materials to the user's skin and/or applying pressure to one or more body parts of the user. Alternatively or additionally, the smart wearable device may be serving as the sensor measuring measurable health parameter of the user (e.g. measuring temperature and/or blood pressure and/or sweating rate and/or any other measurable health parameter of the user), and the health controller device may be responsive to signal from the smart wearable device and configured and operable for initiating the provision of treatment to the user, e.g. by issuing suitable alerts (via communication with the user and/or to other entities) and/or operating other treatment provider modules (such as cardiac pacemaker, insulin injector and/or other treatment provider modules).

In general the composite electronic system may include any number of complementary (compatible) components, where all or some of which may be marked with the OBOC coding scheme of the present invention. However for the sake of clarity and without limiting the scope of the invention, in the following description often discussed and exemplified are only two, first and second, complementary (compatible) components of the system, which are marked by the OBOC scheme of the present invention.

According to the OBOC marking technique of the present invention, at least two complementary/compatible components of the composite electronic system are marked by respective XRF identifiable marking compositions, which are coded to respectively carry/encode complementary XRF signatures, which may be similar—and/or matching—and/or corresponding—XRF signatures that are readable by XRF techniques. The first and second complementary/compatible components, which are marked by the XRF markings of complementary (similar/matching/corresponding) signatures, may for example include: (i) the electronic circuit board of the composite system and at least one electronic component mounted/connected thereon/thereto; and/or (ii) the packaging of the composite electronic system (e.g. the packaging of a chip) and the integrated circuit thereof (e.g. the die); and/or (iii) a first and second separated modules/devices of the composite system (e.g. a controller device and a smart wearable garment) which may be connectable to one another by wires or wirelessly.

In this regards it should be noted that the phrase similar signatures is used herein to specifically designate a case in which the XRF spectral response of the XRF marking of the two components of the composite system are similar in at least a predetermined portion thereof (e.g. at least one spectral part thereof), and/or that they are indicative of similar marking compositions. To this end, the similar XRF signatures may pertain to the similar concentrations of the active, XRF responsive, marker elements in the respective substrates from which the respective XRF signals carrying the signatures were emitted, but may have different actual XRF spectra due to the effects of the substrate (material and/or texture) to which the XRF marking is applied and/or due to the technique by which the marking is applied to the substrate. The phrase matching signatures is used herein to specifically designate a case in which a match between the signatures can be determined by processing the XRF signatures based on a certain predetermined formula/constraint to determine whether they are complementary (whether there exists a matching between them, e.g. without a need for utilizing external reference data to associated). In this sense, the similar signatures are a particular case of matching signature in which the match constraint is equality between them. Another way for determining a match between to signatures (after translating them to numerical values) is for example to check whether their addition sums up to a predetermined check sum value. The phrase corresponding XRF signatures is used herein to designate the case where a correspondence between the signatures can be verified by any suitable technique (e.g. utilizing reference data such as a lookup table (LUT) defining the correspondence between signatures. To this end matching signatures are generally a particular case of corresponding signatures, in which the match is determined by a predetermined relation between the signatures, thus not requiring use of external reference data.

The marking technique and the coding system of the present invention may be utilized in manufacturing customized electronics (custonomics) and personalized electronic components. For example, the code in a circuit embedded in a smart garment (e.g. for medical use), and the garment itself may be marked by a code associated with an individual. Such a smart garment for example may be custom made for a person with a medical condition (e.g. as a medical prescription) and the XRF marking may be used to verify that the customized garment is supplied to the right person.

The XRF marking can be used for the following purposes:

Anti-counterfeit measure wherein the circuit board and various components may be marked. In particular, the XRF marking can be used for verifying, during the assembly, that the components to be assembled on the circuit board are 'authentic' and were manufactured by the original manufacturer. This aspect of the invention may provide authenticity and security measure for suppliers and end users as well. For example, upon receiving a circuit board the user can use the marking to authenticate the source, or type of the various components. Additionally, the marking allows the user to hand over the possession of the circuit (e.g. for repair or upgrade) and have the ability to verify that the circuit was not tampered with, for example the user can verify that none of the components has been replaced and that only authorized components have been installed. In addition, the marking can be used for verifying that the component is assembled at 'correct' position on the circuit board.

A component manufacturer can verify using such markings that the components are getting to the 'right' destination in order to prevent unauthorized trade of his components.

Supply chain management and control of supply chain diversion wherein the marking may include information relevant to the control of supply and production activities. For example, a number of marking composition may be applied at different stages of production and/or supply providing indication of the current production stage.

Manufacturer of smart clothing (wearable devices) can use such marking of one or both the garment (wearable object) and the circuits and electronic components which are to be assembled/attached to the garment are authentic and compatible. In particular, such marking may be of crucial importance in smart wearable objects that are used for medical purposes (see for example US 2016/0022982), wherein both the garment and the circuit board usually have special properties (the garment for example may include conductive threads) and must be of high quality.

The marking composition may be applied to the circuit board and the components at a single location or alternatively at different facilities. For example, the XRF markings of the components of the PCB may be applied at the facility of the of an authorized manufacturer. These marking may be read at the assembly facility of the circuit board authenticating the origin of the components.

The entire circuit and its components may be marked by same composition/the same XRF-signature/code-word. Alternatively, the various parts or components may be marked by the different code words of the same XRF-signature/code. For example, an XRF signature of a component may include a prefix containing information associated with the circuit board as a whole (indicating, for example the type of the circuit, the date of assembly, the destination or the client to which the circuit is to be sent) and a suffix including information associated with the component (type of component the manufacturer, the date of manufacturing, and so on).

The coding system associated with the marking may also include localized marking in different locations on a circuit board and/or on a single component, such that the configuration of the locations of the marking constitute part of the code. Namely, the specific locations of the markings would be incorporated in the code word associated with the marking. In other words, in some embodiments of the present invention the method/system (e.g. XRF reader) for reading the marking includes operating means, such as an imager and/or image recognition means) for identifying and determining the location of the marking on the marked component (on the marked circuit board), and for determining the code word read from the marking based on both (i) the XRF signal obtained from the marking; and (ii) the location of the marking on the marked component.

For the purpose of controlling the chain of supply (e.g. controlling unauthorized supply chain diversion) a number of marking compositions (each with a different XRF signature) may be applied to the circuit board at a number of location along the chain of supply or the assembly line such that reading the XRF markings provides information relating to the assembly of the circuit.

The XRF marking composition applied to a circuit board or to its components does not interfere with the electric or magnetic properties of the board or its components. Also the XRF marking composition may be configured such that it does not alter the appearance of the circuit board such that other legends markings and logos are not affected by the application of the marking composition (e.g. it may be by itself transparent and/or it may be embedded invisibly into the marked substrate material of the component).

The marking composition may also be applied to flexible circuits which may be included in wearable products and smart clothing used for medical purposes, fitness and workout as well as fashion and lifestyle. For example, smart shoes measuring biomechanical data, smart clothes that adjust to outside temperature and/or a garment that includes sensors measuring biometric indicators such as heart rate, skin moisture, and skin temperature. Smart garments may also be used for therapeutic purposes such as delivering electric shocks to the heart in case of cardiac arrest.

The smart garment may comprise of special materials and fabrics (for example breathable fabrics or fabrics which include conductive threads) and may be manufactured by different manufacturers.

The marking composition in this case may be applied to both flexible circuit (e.g. flexible circuit board), and to the fabric, authenticating both components. In addition, the marking may be used for quality control and control of chain of supply wherein only fabrics and associated circuit marked by suitable XRF signatures or codes may be assembled/combined together.

Thus according to a broad aspect of the present invention there is provided an electronic system including a plurality of components comprising at least a first and a second electronic components. The first electronic component includes a first XRF marking composition configured for emitting a first XRF signal having a first XRF signature in response to irradiation thereof by XRF exciting radiation.

The second electronic component includes a second XRF marking composition configured for emitting a second XRF signal having a second XRF signature in response to irradiation thereof by XRF exciting radiation. The first and second XRF markings are respectively configured such that the first XRF signature of the first electronic component corresponds to the second XRF signature of the second electronic component thereby enabling verification that said first and second electronic components are respectively compatible components of said electronic system.

According to another broad aspect of the present invention there is provided a method for verifying compatibility of components of an electronic system that includes at least a first and a second electronic components. The method includes:
- providing a first component and a second components presumably associated with the electronic system;
- irradiating the first and second components with XRF exciting radiation;
- detecting one or more XRF response signals emitted in response to said irradiating from the first and second components;
- processing the one or more XRF response signals to identify a first and a second XRF signatures associated respectively with first and second XRF marking compositions on said first and second components;
- upon identification of the of the first and second XRF signatures, processing said first and second signatures to determine a correspondence between them, and verifying a verifying compatibility of said first and second components to the electronic system based on said correspondence.

It should be noted that in various embodiments and implementations of the present invention the marked components of the system may include respectively different substrates to which the XRF markings are applied. Accordingly there may be a need for calibrating the XRF measurements performed on different components of different substrates.

Therefore according yet another broad aspect of the present invention there is provided a method for calibrating XRF measurements of XRF markings applied to one or more substrate materials. The method includes carrying out the following:
- providing plurality of samples of including samples of various substrate material and various XRF marking compositions of different concentrations of XRF marker elements on the various substrate materials;
- interrogating the plurality of samples of the particular substrate material by an XRF analyzer to determine for each sample a counts per second (CPS) value indicative of photons of a certain energy range(s) associated with the XRF marking elements;
- determining and storing calibration data XRF for use on measurements of XRF markers applied to said substrate materials, whereby said calibration data includes data associating the predetermined/a-priory-known concentration of the XRF marker elements in the plurality of samples with the corresponding CPSs obtained from the respective samples. In this case, the calibration data may be used to determine the code-word of the marking based on the CPSs obtained from each sample.

Alternatively or additionally, the calibration procedure may include determining the XRF response spectra (e.g. the CPSs) obtained from a sample of a predetermined substrate (e.g. having known material and possibly known texture) to which a certain predetermined marking composition has been applied, and recording that XRF response as the code-word associated with the marked substrate, i.e. marking of the predetermined substrate by the predetermined marking composition. In this case, the XRF response spectra itself (possibly together with additional information such as the location of the marking on the object being marked) may represent the code word associated with that predetermined marking while on/in that predetermined substrate. That is, in this case the code-word is not related and not directly indicative of the concentrations/relative-concentrations of the marking elements, but is also associated with and affected by the properties of the substrate and the marking application technique, i.e. the unique XRF signature is formed by a combined response of the marked substrate to predetermined "reading" (exciting) radiation. For example, a lot of similar objects/substrates (i.e. objects produced by the same technique and having the same or very similar material composition and layout) may be associated with (identifiable by) the same reference/calibration XRF signature. Such signature is determined as stored to serve the reference one, upon applying the marking to one of the objects (or test object) and reading the XRF response therefrom.

Also in certain implementations the method also includes performing an SNR optimization step which is carried out by applying XRF interrogations with different XRF parameters, to said plurality of samples, to determine an optimized set of XRF parameters which optimizes an SNR of the XRF measurements of that substrate materials, and optionally storing said optimized set of XRF parameters in the calibration data.

According to further yet another embodiment of the present invention there is provided an XRF reader including an XRF analyzer for interrogating an object and detecting an XRF response signal indicative of a spectral XRF signature of a marking composition applied to the object; and a signature calibration module associated with calibration data indicative of a correspondence between spectral XRF signature and concentrations of XRF marking elements of said object at which said XRF marking elements are included. The signature calibration module is adapted to utilize said spectral XRF signature to determine concentrations of XRF marking elements in said object based on the calibration data.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1:
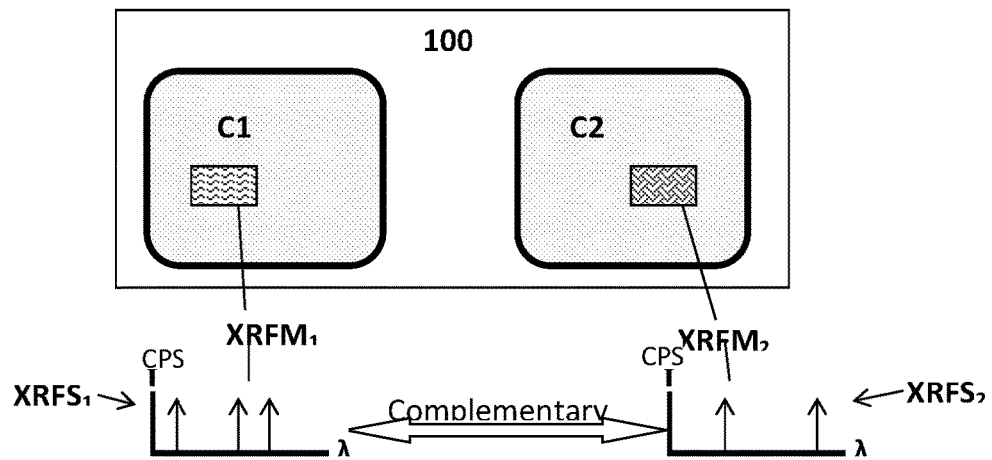
FIG. 1 is a block diagram of an electronic system according to an embodiment of the present invention including a plurality of components marked by XRF marking compositions.

Reference is made to FIG. 1 which shows a block diagram of an electronic system 100 which includes a plurality of components marked by XRF markings. In this specific example the electronic system 100 is illustrated with two components C1 and C2 (herein after referred to as the first and second electronic components) that are respectively marked by XRF respective first and second marking compositions $XRFM_1$ and $XRFM_2$ associated with XRF signatures. It should be understood that generally more than two components marked with XRF marks may be included in the system 100.

In various embodiments of the present invention the components C1 and C2 may include electronic components of the electronic system 100, such as a circuit board and electrical components mounted thereon, and/or the components C1 and C2 may include separate devices of a distributed electronic system 100, such as a control unit/device and a smart wearable device constituting together the system 100, and/or the components C1 and C2 may include an electronic module and a casing/packaging/enclosure thereof. Also, in various embodiments of the present invention the first and second XRF marking compositions $XRFM_1$ and $XRFM_2$ on the components C1 and C2 may be marks indicative of one or more of the following: the brands of the respective components C1 and C2, the manufacturing details (e g manufacturer, manufacturing place manufacturing date, LOT number, etc') of the components C1 and C2, and/or indicative of the identification of the individual components such as serial numbers of the components C1 and C2. Accordingly the XRF marking compositions $XRFM_1$ and $XRFM_2$ provide elemental identification of the components (e.g. their serial numbers brand and/or manufacture).

It should be noted that in various embodiments of the present invention the XRF markings $XRFM_1$ and $XRFM_2$ are applied to (e.g. applied on and/or embedded/blended) within different substrate materials in the different components (e.g. one component may include a polymer substrate at which the XRF marker in included while the other may include natural fibers serving as the substrate at which the XRF marker is included). In this regards the terms substrate and/or substrate materials is used herein to indicated the base material (e.g. media/substrate material) of the component of the electronic system with the XRF marking composition is applied/embedded. Accordingly the marking compositions of different components may include different promoters and/or different binder materials in accordance with the substrate to which the marking composition is to be applied in the different components of the system.

In this example the first electronic component C1 includes a first XRF marking composition $XRFM_1$ configured for emitting, in response to irradiation thereof by XRF exciting radiation, a first XRF signal a first XRF signature $XRFS_1$. The second electronic component C2 includes a second XRF marking composition $XRFM_2$ configured for emitting a second XRF signal having a second XRF signature $XRFS_2$ in response to irradiation thereof by XRF exciting radiation.

According to the present invention the first and second XRF marking compositions, $XRFM_1$ and $XRFM_2$, are respectively configured such that the first XRF signature $XRFS_1$ obtained from the first electronic component C1 corresponds to the second XRF signature $XRFS_2$ from the second electronic component C2. The XRF marking compositions, $XRFM_1$ and $XRFM_2$, thereby provide elemental identification codings enabling verification that the first and second electronic components are respectively compatible components (e.g. complementary components) of the electronic system. The elemental identification, which is elemental in the sense that it is based on markings associated with elements (herein after also referred to as active XRF elements to indicate chemical elements that emit X-Ray Fluorescence in response to irradiation thereof) embedded in the components C1 and C2, may be, for example, used-for/ facilitate brand protection, authentication of customized electronics, providing liability of electronic components in medical devices (e.g. in particular in wearable medical devices), and providing bridge liability for the coupling between virtual services or products and physical operational systems (for example the coupling between personal data and a smart clothing).

FIG. 1 also shows a table, Table 1, exemplifying possible relationships between the XRF signatures, $XRFS_1$ and $XRFS_2$, of complementary marks, $XRFM_1$ and $XRFM_2$, used for marking complementary/compatible components, C1 and C2, of the electronic system 100 according to the present invention. In this regards, it should be understood that although only two components, C1 and C2, are exemplified in this figure, system 100 may include any number of plurality of XRF marked components with the relationship between their marks similar to those exemplified in Table 1.

More specifically, in certain embodiments of the present invention the XRF marking compositions, $XRFS_1$ and $XRFS_2$, on the respective components, C1 and C2, of the system 100, are configures such that a correspondence between the first and second XRF signatures, $XRFS_1$ and $XRFS_2$, of the XRF signals emitted therefrom in response to XRF exciting radiation (e.g. exciting radiation obtained by illuminating the system or its components by X-Ray or Gamma-Ray radiation) is based on a match between the XRF signatures, $XRFS_1$ and $XRFS_2$. More specifically a match can be determined by utilizing/providing a certain predetermined mutual relationship condition (e.g. Function $(XRFS_1, XRFS_2)$<or=or>VALUE) between the XRF signatures, which should be satisfied by the XRF signatures $XRFS_1$ and $XRFS_2$ in cases there are matching. For instance, as exemplified in row 2 of table 1, the condition Function $(XRFS_1, XRFS_2)$ is that the superposition/addition of the signatures $XRFS_1$, $XRFS_2$ equals a certain cumulative signature CXRFS, namely the following condition should be satisfied in this example:

$$\text{Function}(XRFS_1, XRFS_2)=XRFS_1+XRFS_2=CXRFS.$$

Indeed other mutual condition may also be used—for example that a difference $XRFS_1-XRFS_2$ between the signatures equals a certain value, and/or that the signatures are similar $XRFS_1=XRFS_2$. The latter case, similarity between the signatures $XRFS_1$ and $XRFS_2$, being a particular case of a matching between them is exemplified in row 1 of the table 1.

It should be noted that embodiments of the present invention in which the correspondence between the signatures, $XRFS_1$ and $XRFS_2$, is determined by matching them utilizing a predetermined condition, such as similarity between the or other, may be advantageous in certain implementation in which in situ verification that components C1 and C2 are compatible/complementary (e.g. in-situ in the sense that there is no need for utilizing external reference data for associating the signatures of complementary components, but only providing a predetermined mutual relationship condition (e.g. similarity) that should be satisfied thereby. Accordingly an XRF verification reader (e.g. such as that exemplified in FIG. 5B), may be furnished with a memory storing the predetermined condition, and may utilize that condition to examine the components of the system, and determine, in situ, whether two or more components of an electronic system are complementary or compatible, without a need for accessing external data sources.

Alternatively or additionally, the electronic system, a correspondence between the first and second XRF signatures is determined based on a reference data (e.g. lookup table (LUT)), such as the REFERENCE-LUT in table 1, associating the XRF signatures of complementary/compatible components, C1 and C2, of the system 100. This is illustrated in self-explanatory manner in row 3 of table 1 in the figure. Indeed in this case the reference data may also be included in a memory/storage of an XRF verification reader (e.g. such as that of FIG. 5B) to enable in-situ verification operation, however, in that case the memory storage may need to be updated at each time additional components/systems with different complementary markings are released.

It should be generally understood that the terms XRF signatures are used herein to indicate at least one portion/region of the spectral response of the components, e.g. C1 and C2 of the system 100 to XRF exciting radiation, which is associated with at least a part of the spectral band at which XRF signals are expected (and not necessarily the entire XRF spectral band). Accordingly, XRF signatures of interest, $XRFS_1$ and $XRFS_2$, may be "hidden" at certain designated spectral regions of the entire XRF response obtained from the XRF marking $XRFM_1$ and $XRFM_2$.

The XRF markings according to the present invention may be applied to various substrates including metals, plastic and fabrics. The novel marking technique of the invention is highly generic, insensitive to materials and structure of the objects (components of the system 100) to which marking, and thus permits verification of authenticity of a great variety of types or components of the electrical system 100, (e.g. circuit boards, electronic components, and fabrics). According to some embodiments the present invention, the present invention also provide a calibration technique and an XRF reading system optionally utilizing this calibration technique enabling to accurately read XRF markings which are applied to different types of substrate materials of different components of the system. This is illustrated for example in FIGS. 5A and 5B which are further described below. Accordingly, the XRF marking technique of the present invention may be insensitivity to the different substrate/materials of the components to which the XRF markings may be applied in the system 100.

The XRF markings (also referred to as marking composition) applied to a component (object) generally includes a low concentration of a marking system, which typically comprises a plurality of marker materials (herein "markers"). Each of the markers being XRF sensitive/responsive in the sense that they emit an X-Ray response signal in response to interrogation (irradiation) by X-Ray or gamma ray radiation.

In certain embodiments of the invention one or more of the marker composition(s) used in the system 100 include at least one XRF-sensitive marker (which is also referred to herein as XRF responsive marker element and/or active XRF marker) and at least one surface binding material (permitting association of said marker to at least a surface region of an object, e.g., a binder material and/or an adhesive material). In certain implementations the concentration of the at least one marker is between 0.1 and 10,000 ppm. In some embodiments, the composition is suitable for application onto at least one region of a surface of the component e.g. C1 or C2 of the electrical system 100.

In certain embodiments the XRF marking composition that is used for marking one or more of the components C1 and C2 includes at least one XRF-sensitive marker, at least one surface binding material, and may also include at least one adhesion promoter and at least one etching agent. The concentrations or amounts of the marker(s) and the binding material(s) within any marking composition of the invention may be set according to a preselected code, which can be measured by XRF analysis, after application of the composition onto the component of the system. In general, the marking composition may include one or more markers with concentrations within the range of 0.1 to 10,000 ppm.

In certain embodiments of the present invention, the marker composition which is used for marking one or more of the components of the system 100 includes a plurality of XRF marker elements, each being present in different concentrations or form. This may be used to provide a unique signature of the marking composition with spectral features characteristic not only of the specific elements in the combination but also of their concentrations or relative concentrations.

Alternatively or additionally, in some embodiments of the present invention, each marking composition that is to be used is prepared with a certain (possibly unique) concentrations of the marking elements (which may be determined/set arbitrarily and possibly event not measured). Then, only after the marking composition is applied to a predetermined substrate (e.g. a sample substrate having certain material and/or texture) by a certain application technique (e.g. CVD, PVD and/or embedding, as described below) the XRF response is read from the marking that is applied to the specific substrate, and that XRF response is set as the code-word of the marking on that substrate. In this case the concentrations of the marking elements are not determined a-priory based on a preselected code, but instead, the code is determined/measured post-priori only after the marking composition (possibly including arbitrary concentrations of marking elements) is applied to the sample substrate. In other words here the code word may be considered to be associated not only with the marking composition but also with the substrate to which it is applied.

Thus, the concentrations and/or relative concentrations of the marking elements may or may not be determined apriority based on the desired code word of the marking, but in some cases the code words is determined post-priory only after a marking composition having certain (not necessarily known) concentrations of elements applied to an object (e.g. a reference object/component) of the type/material similar to that of the component that is to be marked by the marking composition. Then, during a calibration process, the XRF spectra (signal/signature) of the marking composition after being applied to the marked object (e.g. to the reference object) is measured, to determine the code word of the marking. This is because, in some implementations, the XRF spectra/signature is not only affected by the concentrations of the marking elements in the marking composition, but may also be affected by the material composition of the object itself being marked and/or by the method of application of the marking composition to the object/component. Accordingly, it should be understood that in such implementations the code-word of the marking, although being affected by the concentrations of the marker elements, may not be indicative of the concentrations of the marking elements and may not be constituted by those concentrations, but may be affected also by additional factors such as the material of the object being marked, the method of application of the marking to the object, and possibly also the location of the marking on the object as indicated above. To this end, two different objects marked by the same marking compositions may yield different code-words.

The XRF marker(s) in a marker combination or independent of other markers in an XRF marking composition may be in a metal form, a salt form, an oxide form, a polymer comprising (in a chemical or a physical interaction) the one or more XRF marking elements, an organometallic compound, or a complex which includes one or more of the XRF marking elements.

In some embodiments of the present invention the surface binding material used in compositions of the invention is a material which binds or promotes binding of the marker to a surface of an object. The at least one surface binding material may be a single material or a combination of materials, which independently or in combination permits irreversible association of the marker/marker combination or any other component of the marking composition to a surface region. The at least one surface binding material is one or more of a binder material, an adhesive material, an adhesive promoter material, a polymer and a pre-polymer, as known in the art. For instance in some implementations, the at least one surface binding material is at least one binder and at least one adhesion promoter. Alternatively or additionally in some implementations, the at least one surface binding material is at least one binder material and/or at least one adhesion promoter, independently of the other, or in combination promote binding of the marker material or any component of the marking composition to the surface of the object.

The etchant or etching agent is selected to cause surface modifications to improve adhesion or generally association, being optionally irreversible, of the marking composition to the surface region of the object.

The following table, Table 2, specifies possible chemical compositions of XRF markings which may be used according to the present invention for marking various components of the electronic system 100.

| Markers | Binder | Adhesion promoter | Etching agent |
| --- | --- | --- | --- |
| Elements with an identifiable XRF signature | thermoplastic polyurethane | Chlorinated Polyolefin | Fumaric acid |
| | thermoplastic polyurethane | Ethylene butyl acrylate copolymer functionalized with maleic anhydride (MAH) | Halogen base acid |
| | poly-ether-urethane | Styrene ethylene butylene block copolymer functionalized with maleic anhydride | Carboxylic acid |
| | polyethylene-terephthalate | Ethylene octen copolymer functionalized with maleic anhydride | |
| | polybutylene-terephthalate | copolymerizable olefinic monomer | |
| | polyvinyl-acetate | Functionalized polyolefins Functionalized ethylene-vinyl-acetate copolymers | |
| | epoxy-acrylate | Functionalized ionomers | |
| | Epoxy | Functionalized polyalkylene oxide polyester block copolymer | |
| | Urethane | Functionalized derivatives of carboxymethylcellulose | |
| | acrylate | Homopolymers and copolymers derived from dicarboxylic acids, diamines and aminocarboxylic acids | |

Figure 2A:
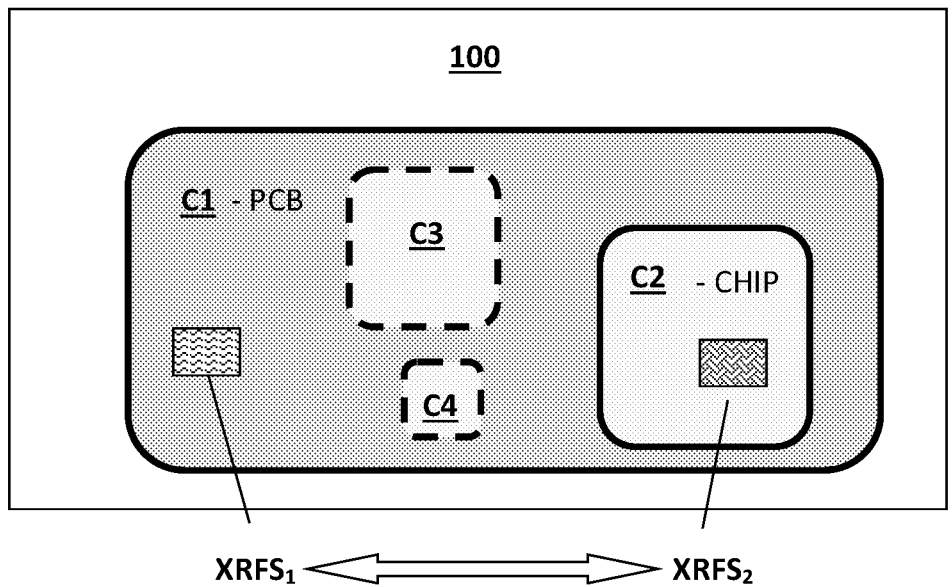
FIGS. 2A to 2D are block diagrams illustrating electronic systems configured according to various embodiments of the present invention which include XRF marking compositions embedded/applied to various components thereof.

It should be noted that additional possible XRF marking compositions, including XRF marking compositions which may be particularly suited for marking metal objects/substrates are described for example in PCT application No. PCT/IL2017/050121, which is assigned to the assignee of the present application, and included herein by reference. Reference is now made to FIG. 2A showing an electronic system 100 configured according to an embodiment of the present invention. It should be noted that here and in all of the figures of the present application described in the following, similar reference numerals are used to designate similar/like elements/method-operations having the similar configurations and/or functionalities.

In this example the first component C1 of the system 100 is an electronic circuit board PCB (which may be rigid or flexible circuit board) and the second component C2 is a component (e.g. electronic component) associated with a designated place on the circuit board C1. Additional components, C3 and C4, which may be also mounted/mountable on the first component C1 (circuit board PCB) and which may or may not include XRF markings, are also exemplified in the figure.

In various implementations of the system 100, the first marking composition XRFM$_1$ is embedded in/on the circuit board PCB by utilizing one or more of the following:

(a) The first marking composition XRFM$_1$ may be blended with the polymers comprising the solder mask applied to the circuit board PCB during its fabrication. For example embedding the XRF marker elements in solder mask based on epoxy and epoxy-acrylate polymers, and\or in photoimageable solder mask (LPSM) inks, and/or in liquid photoimageable solder mask commonly called LPI or LPISM; and\or in dry film photoimageable solder mask (DFSM).

(b) The first marking composition $XRFM_1$ may be blended with ink of prints (e.g. logos/legends and so forth) which may be printed on the circuit board PCB. For example by mixing/embedding XRF marker elements with one or more of the following: UV cure polymer or thermal cure polymers inks, such as epoxy or urethane, or acrylate polymers, which are applied as silk screen printing or as liquid photo polymers or as ink jet printing. Alternatively, the marking applied to the surface of the circuit board may be an invisible composition.

(c) The marking composition may be dispensed or deposited the onto the surface of the object by various additional techniques such as printing (such as ink jet printing), stamping, spraying, injecting, brushing, and air brushing.

(d) Alternatively or additionally, the marking composition may be applied to the surface of the circuit by vacuum deposition methods wherein the deposition process is carried out at pressure which is well below atmospheric pressure or in vacuum (i.e. in a vacuum chamber). Preferably, the vacuum deposition process which may be used in such marking techniques utilizes Chemical Vapor Deposition (CVD) including various processes such as low-pressure chemical vapor deposition (LPCVD), Plasma-Enhanced Chemical Vapor Deposition (PECVD), Plasma-Assisted CVD (PACVD), and Atomic Layer Deposition (ALD). Alternatively, or additionally, the process of depositing the marker material(s) on the object includes Physical Vapor Deposition (PVD) in which the vapor source is solid or liquid. A PVD process may use techniques such as sputtering, cathodic arc deposition, thermal evaporation, laser ablation serving as a (solid) precursor to generate vapor, and electron beam deposition, to generate the deposited particles in a vapor phase.

(e) The first marking composition $XRFM_1$ may be blended with the compounds comprising the under-fill binding of one or more components to the circuit board PCB. For example, blending the XRF marking elements with under fill adhesives based on low viscosity epoxy polymers, and/or with urethane polymers, and/or with acrylate polymers.

(f) The first marking composition $XRFM_1$ may be blended with polymers of the packaging of some of the components on the circuit board PCB. For example, blending the XRF marking elements with Thermoset Electronic Polymers (such as: Epoxies, Polyimides, Silicones, Phenolics, Polyurethanes) and/or with Thermoplastic Polymers (such as: Polysulfone, Polyethersulfone, Nylon 66—polyamide, Polyphenylene Sulfide, PBT—Polybutylene Terephthalate, PET—Polyethylene Terephthalate).

(g) The marking composition $XRFM_1$ may be embedded in an overly, or coating, of the solder mask or of components of the circuit board PCB. For example, the overly, or coating may include: thermoplastic polyurethane, thermoplastic polyurethane, poly-ether-urethane, polyethylene-terephthalate, polybutylene-terephthalate, polyvinyl-acetate, epoxy, epoxy-acrylate, urethane, acrylate based polymers.

(h) The marking composition $XRFM_1$ may be blended with polymers applied to through vertical interconnect access (VIA) holes on the circuit board PCB. For example, XRF marker elements blended in polymers based on low viscosity epoxy polymers, or urethane polymers or acrylate polymers (i) The PCB may include a special 'fake' component mounted thereon for carrying the marking composition $XRFM_1$, and the marking composition $XRFM_1$ may be contained/carried on/at the special 'fake' component according to any one of the techniques described above.

In this embodiment, the second component C2 may be for example an electronic component, such as a chip, that is mountable on the circuit board PCB. The second marking composition $XRFM_2$ may be embedded in the electronic component C2 in one or more of the following:

(a) The second marking composition $XRFM_2$ may be blended with ink of prints printed on the electronic component. The chemical composition of the marking composition $XRFM_2$ may be this case similar to the ink marking composition described above with regards to $XRFM_1$.

(b) The second marking composition $XRFM_2$ may be blended with polymers of the packaging of the second component C2. The chemical composition of the marking composition $XRFM_2$ may be this case similar to marking composition $XRFM_1$ applied to the polymers of the PCB as described above.

(c) The marking composition $XRFM_2$ may also alternatively or additionally be blended with polymers applied to through vertical interconnect access (VIA) holes of the second component C2.

Figure 2B:
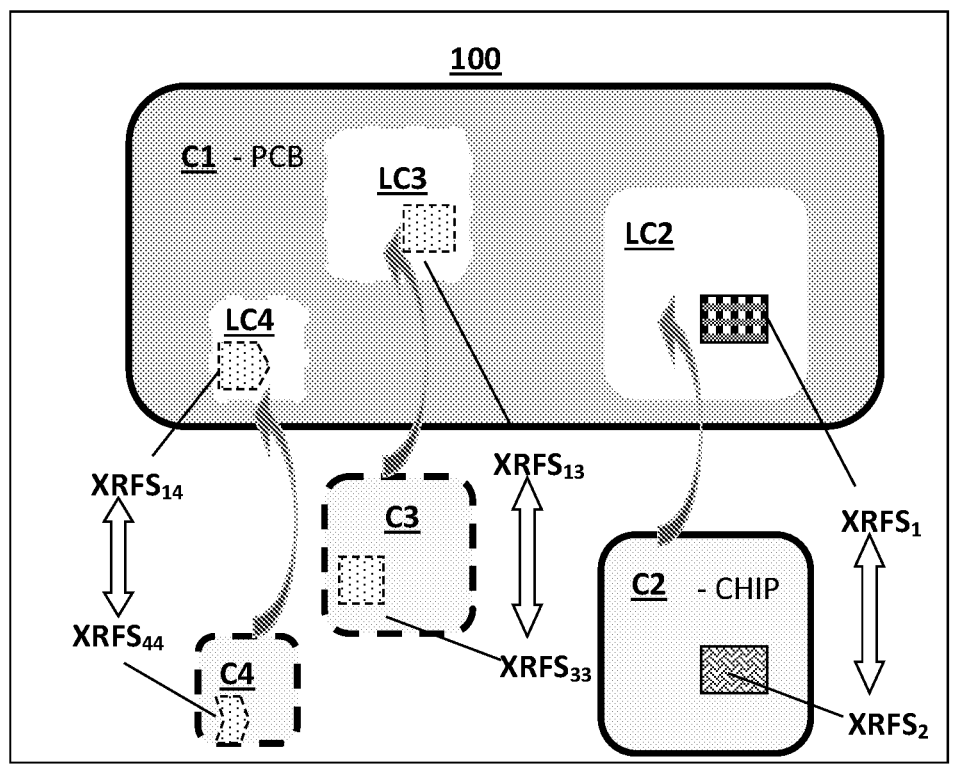

Reference is now made to FIG. 2B showing an electronic system 100 configured according to another embodiment of the present invention, and in which the first electronic component C1 is a printed circuit board PCB, and the second component is an electronic component mountable on the circuit board PCB at a designated location LC2. Here, the first XRF marking $XRFM_1$ is spatially located on the PCB at the designated location LC2 at which the second component C2 should be mounted on the circuit board PCB. This thereby enabling to utilize a scanning (e.g. spatially focused) XRF analyzer to scan the circuit board PCB to identify the designated location LC2 for mounting of the second component C2, based on a correspondence (e.g. match or similarity) between the first and second signatures, $XRFS_1$ and $XRFS_2$ of the first and second XRF markings $XRFM_1$ and $XRFM_2$. The may be used to determine/verify the proper placement location LC2 of the second component C2 on the circuit board PCB.

Optionally, as also illustrated in FIG. 2B, the designated location LC3 and LC4 at which to mount additional components C3 and C4 of the system 100 are also marked with respective XRF marking compositions $XRFM_{13}$ and $XRFM_{14}$. Accordingly, the components C3 and C4, which are also illustrated in the figure, are also marked with the at which the XRF marking compositions $XRFM_{33}$ and $XRFM_{44}$ which respectively correspond to the XRF marking compositions $XRFM_{13}$ and $XRFM_{14}$ on the PCB. Accordingly this enables to utilize the scanning XRF analyzer to scan the circuit board PCB to determine/verify the proper placement locations for the components C2, C3 and C4 prior or after their assembly/mounting on the PCB and thereby enable, either automatic assembly of the electronic system 100, and/or enabling carrying out quality assurance (QA) checks on the assembled system 100, to verify proper placement of compatible components in their proper locations.

Figure 2C:
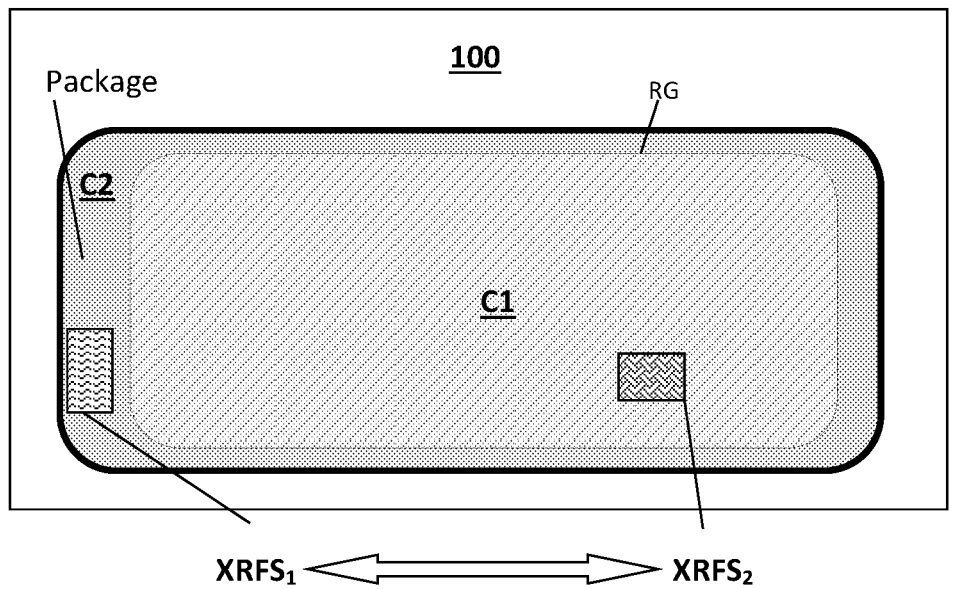

Reference is made to FIG. 2C showing an electronic system 100 according to another embodiment of the present invention in which the first component C1 marked by the XRF marking composition $XRFM_1$ is an electronic component and the second component C2 marked by the XRF marking composition $XRFM_2$ is a casing/packaging of the electronic component C1. The electronic component C1 may be located/enclosed within the packaging C2, and accordingly in the figure a region RG of the packaging is illustrated semitransparent to reveal the XRF marking XRFM$_1$ of the electronic component C1.

For example the electronic system 100 may be in this case a chip (e.g. assembled chip), whereby the first component C1 may be a semiconductor die of the chip 100 and second component C2 may be a package of the chip 100 which encloses the die C1.

Accordingly the package may be for example made of, or may include polymer materials and the second XRF marking composition XRFM$_2$ may be embedded in the polymer materials of the package C2 in the manner described above for embedding XRF marks in polymers, or it may be included/embedded in an under-fill material in between the die and the package. The first XRF marking composition XRFM$_1$ may be in this case embedded/included in the material of electrical inter-connect (e.g. indium bumps) and/or in the material fillings VIA holes of the die C1, To this end according to certain embodiments of the present invention the first and second XRF marking compositions, XRFM$_1$ and XRFM$_2$ are selected/configured such that in response to irradiation of the system by XRF exciting radiation, they emit together a composite XRF signal (e.g. referenced CXRFS in FIG. 1) including the first and second XRF signals from both the components C1 and C2. The XRF marking compositions, XRFM$_1$ and XRFM$_2$, (specifically the contents of active XRF responsive materials therein) may be specifically selected/configured such that the composite XRF signal CXRFS is indicative of the first and second XRF signatures XRFM$_1$ and XRFM$_2$ (namely that the first and second XRF signatures XRFM$_1$ and XRFM$_2$ can be distinguishably identified therein), and such that the first and second XRF signatures XRFM$_1$ and XRFM$_2$ do not interfere with one another (e.g. such that they complement on another) in the composite XRF signal CXRFS. This may be achieved for example by respective configuration of the first and second XRF marking compositions, XRFM$_1$ and XRFM$_2$, with specifically selected set of active XRF responsive materials in each of them such that the spectra (set of wavelengths $\{\lambda_i\}$) in their respective XRF signatures XRFS$_1$ and XRFS$_2$, are mutually exclusive (e.g. the do not emit/have XRF spectral response peak at the same wavelength). This is illustrated for example in row 2 of table 1 in FIG. 1 showing the signatures XRFS$_1$ and XRFS$_2$ having mutually exclusive spectral peaks. Accordingly the signatures XRFS$_1$ and XRFS$_2$ do not interfere with one another and can be read together to determine whether the components C1 and C2 (e.g. the inner component C1 and the outer component enclosing it C2) are compatible components (e.g. and whether the system 100 is authentic). In this regards, it should be noted that since the XRF technique is used, which is generally based on irradiation and detection of X-Ray or Gamma-rays, determining whether the component is authentic can be done non-invasively without opening the package/casing C2 (e.g. by irradiating the entire system with X-Ray or Gamma-rays and detecting the composite XRF signal CXRFS emitted therefrom in response).

Figure 2D:
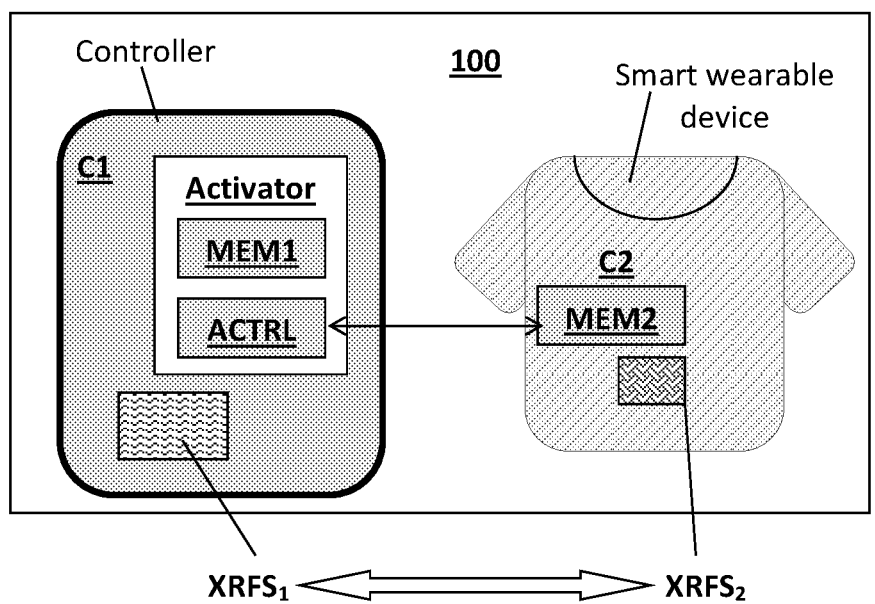

Reference is now made to FIG. 2D showing an electronic system 100 according to yet another embodiment of the present invention. In this embodiment the first and second electronic components C1 and C2, are generally first and second electronic devices each associated or includes a respective data storage module MEM1 and MEM2, and at least one of them includes, or is associated with a pairing and activation controller ACTRL capable of connecting to both the memory/data storage modules MEM1 and MEM2. The memory modules may be for example in the form of computer memory modules, flash memory, RFID module and/or any other usable data carrying/storing module device.

To this end in this example the first component C1 is a first electronic device including a first data storage module MEM1 (hereinafter without loss of generality referred to also as memory) capable of storing a first data portion indicative of a correspondence between said first and second XRF signatures XRFS$_1$ and XRFS$_2$. The second component C2 is a second device including a second data storage module MEM2 capable of storing a second data portion indicative of a correspondence between the first and second XRF signatures XRFS$_1$ and XRFS$_2$. In this regards, it is noted that during a pairing operation (e.g. which may be carried out for example at a plant where the first and second devices are paired and/or at the distributor/shop at which they first and/or second device are soled/distributed) may include reading the XRF marking (e.g. XRFS$_2$ of one of the devices) for storing it (or a code corresponding to it) in the memories MEM1 and MEM2 of the first and second devices. Accordingly an elemental ID coding is introduced in to the memories of the first and second devices enabling elemental pairing between them based on the correspondence between their XRF marks. The pairing/activation controller ACTRL is configured and operable for carrying out the following before enabling activation of mutual operation of the devices C1 and C2 (e.g. upon existence of wired or wireless connation between the first and second devices C1 and C2):

(i) accessing the first and the second data storage modules, MEM1 and MEM2, upon wired or wireless connation between the first and second devices;

(ii) retrieving the first data portion from the first memory MEM1 and retrieving the second data portion from the second memory MEM2; and (iii) processing the first and second data portions to determine whether the first component/device C1 is paired with the component/second device C2.

In this connection the processing to determine whether the components/devices C1 and C2 are paired includes determining whether exists based a correspondence between the codes which are stored in the memories MEM1 and MEM2 of the first and second devices. This provides elemental identifications that devices C1 and C2 are compatible and are allowed for working together, which is based on the compatibility of the first and second XRF signatures of the first and second devices (as indicated by the reference data stored in the memories MEM1 and MEM2. To this end the activation controller ACTRL provides/enables conditioned activation of mutual operation of the first and second devices C1 and C2 based on a pairing (elemental pairing) between them.

In this particular example of FIG. 2D one of the devices, specifically the second component C2, is a smart wearable/garment device. For instance the electronic system 100 may be a healthcare system, wherein at least one of the first and second devices, C1 and C2, is configured for monitoring one or more conditions of a user using the system 100, and at least one of the first and second devices C1 and C2 is configured and operable for providing treatment to the user based on the monitored condition. Indeed in this case, since the healthcare system (the monitoring properties and/or the treatment properties) might be customized for use by specific user and might damage other users, it is advantageous to use the elemental pairing between the first and second devices C1 and C2, to thereby provide inherent verification that the correct treatment device (e.g. garment C2) is connected to the correct monitoring device (e.g. C2) of the same user.

According to various embodiments of the present invention the smart wearable device (garment) C2 may include one or more fabrics made with natural and/or synthetic fibers.

In some embodiments the fabric is made/includes with natural fibers the XRF marking composition may be included in the dyes used for dying the natural fibers. Accordingly the active XRF responsive materials may be added to the natural fibers of the fabric in the dying stage of the fabric production.

Typically natural fibers are dyed by utilizing Mordants, whereby herein the term Mordants is used for chemicals which usually have a metal with a valency of at least two or more, (they may also include other types of compound as well). More specifically mordants are mineral salts that bind dyes into fiber (dyes for natural fibers require use of a mordant to fix the pigment to the fabric and prevent the color from fading or washing out). Commonly used mordants for natural dyes include for example one or more of the following: alum, potassium aluminum sulfate, tin and bluevitriol, chrome, potassium dichromate, potassium bichromate, blue vitriol, copper sulfate, ferrous sulfate, stannous chloride, sodium dithionite, sodium hydrosulfite, ammonia hydroxide, cream of tartar, potassium bitartrate, "Glauber's salt", sodium sulfate, lime, lye, sodium hydroxide, oxalic acid, tannic acid, uria, vinegar, acetic acid, washing soda or sodium carbonate. This provides a variety of potential XRF markers which can be used/included in various quantities in the Mordants material used in dying of the natural fibers to thereby obtain a desired XRF signature of the fiber. To this end in natural fabrics/fibers the XRF marking composition (e.g. $XRFM_2$ in the figure) may be included in the Mordants used for dying the fabric and with the Mordants composition specifically selected to provide the desired XRF signature (e.g. $XRFM_2$ in the figure).

Alternatively or additionally the fabric may be made, or may include synthetic fibers made from the polymer materials such as: Linear polyamides (Nylon 6-6, 6-10, 6, 7), Acetate cellulose, Lyocell, Polyester—PET (e.g. Dacron,™ Terylene™), Lycra, Spandex, Kevlar, and Acrylic fibers. In this case dying of the fibers/fabric is performed the production of the fibers of the fabric (typically during the extrusion process). Accordingly XRF marking compositions (e.g. $XRFM_2$) may be in this case introduced into the fiber by during the extrusion process (e.g. by—blending the XRF marker elements with the other materials of the synthetic fibers).

Figure 3:
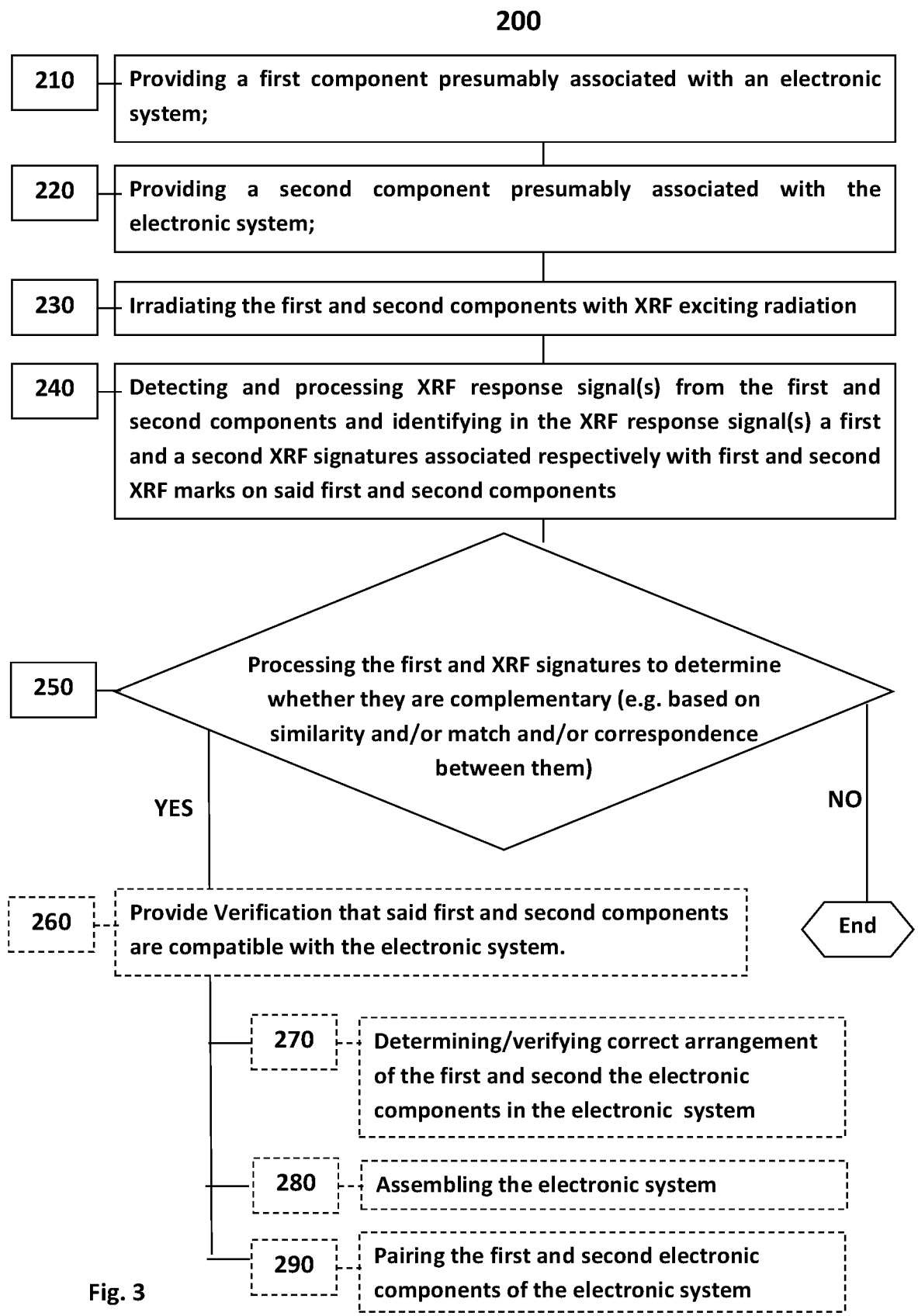
FIG. 3 is a flow chart of a method for verifying compatibility of components of an electronic system according to an embodiment of the present invention.

Reference is now made to FIG. 3 which is a flow chart of a method 200 for verifying compatibility of components (e.g. C1 and C2) of an electronic system (e.g. 100) which includes at least two, first and second, components.

The method includes the following operations:

Operation 210 includes providing a first component C1 that is presumably associated with the electronic system 100.

Operation 220 includes providing a second component C2 that is presumably associated with the electronic system 100;

Operation 230 includes irradiating the first and second components C1 and C2 with XRF exciting radiation. In various implementations of the present invention the irradiation of the components by the XRF exciting radiation (e.g. by X-Ray or Gamma rays) may be performed by separately irradiating separate components, and/or by irradiating both/several of the components together.

Operation 240 includes detecting one or more of the XRF response signals from first and second components, C1 and C2, which are emitted in response to the irradiation of the first and second components, C1 and C2 by the XRF exciting radiation. In this regards it should be noted that dependent of the XRF signatures which are expected to be detected (e.g. whether they are expected to interfere with one another or not), the detection of the XRF response from several/two or more components may be done separately for separate components, or may be done for several components together. Then, the one or more XRF response signals may be processed to identify a first and a second XRF signatures, $XRFS_1$ and $XRFS_2$, which are respectively associated with the first and second XRF marking compositions $XRFM_1$ and $XRFM_2$ on the first and second components, C1 and C2. For instance the processing of the one or more XRF response signals at this stage may include certain signal to noise enhancement and background filtration, to enhance the SNR of the signals. For example, such SNR filtration may be carried out by utilizing the XRF analyzer (reader/system) and/or the method described in PCT patent application No. PCT/IL2016/050340, which is assigned to the assignee of the present application and incorporated herein in its entirety by reference, for removing the trend and/or the periodic spectral components from the detected XRF signals. Also the processing of the one or more XRF response signals at this stage may include filtering certain portions (spectral bands) of the detected signal(s), to leave only those spectral bands at which the XRF signatures of interests $XRFS_1$ and $XRFS_2$ should be found. This provides for identifying/extracting from the detected XRF signals, the signatures $XRFS_1$ and $XRFS_2$ and/or a cumulative/composite signature CXRFS including both the signatures $XRFS_1$ and $XRFS_2$.

Operation 250 is carried out upon identification of the first and second XRF signatures, $XRFS_1$ and $XRFS_2$, or the cumulative/composite signature CXRFS including them both, and includes processing the identified signatures to determine whether exists a correspondence between. The correspondence may be determined based on a similarity between the signatures, and/or based on a matching between them according to a predetermined condition, and/or by utilizing reference data (e.g. LUT) associating corresponding signatures, as discussed above in more details in illustrated in Table 1 of FIG. 1. To this end operation 250 of method 200 may optionally include provision of a certain predetermined condition indicative of a predetermined mutual relationship between matching XRF signatures (e.g. which are complementary/corresponding signatures), and determining whether the first and second XRF signatures satisfy said predetermined condition (this as indicated above enable in situ verification that the first and second components are compatible while obviating a need for using external reference data). For instance the predetermined condition may be that the first and second XRF signatures are similar in the at least one spectral region thereof, and wherein the processing may thus include comparing this spectral region in the first and second XRF signatures $XRFS_1$ and $XRFS_2$. Alternatively or additionally the correspondence between the first and second XRF signatures may be determined based on a reference data associating signatures of compatible components. In this case the processing in 250 includes obtaining the reference data (e.g. from a memory and/or from an external source) and processing the first and second XRF signatures against the reference data to determine whether there is an indication of a correspondence between them a in the reference data.

In case the conclusion in operation 250 is that the detected signatures are not complementary, the components C1 and C2 are thus determined to be not compatible with one another and method 200 may end, while possibly providing/outputting indication that the components are not compatible.

In case the conclusion in operation 250 is that the detected signatures are complementary, the components C1 and C2 may thus be determined to be compatible with one another and/or with the electronic system 100. In this case operation 260 may optionally be carried out to provide/output suitable indication of the compatibility of the components in the system 100 (which may be in turn an indication that the system and/or the components are authentic and not counterfeit system/components).

Accordingly, in this case whereby the components C1 and C2 are compatible with one another (e.g. can be suitably used together in the system 100), additional operations 270 280 and/or 290 of method 200 may optionally be further carried out. For instance, operation 270 may optionally be carried out for determining/verifying correct arrangement of the first and second electronic components C1 and C2 in the electronic system 100. This was described/exemplified above with reference to FIG. 2B and is also further described in more detail with reference to 4A below. Alternatively or additionally, upon identifying that the components C1 and C2 are compatible, operation 280 may be carried out for assembling the electronic system 100 (e.g. possibly based on the locations/arrangement of the components as may be determined in optional operation 270). Yet alternatively or additionally, upon identifying that the components C1 and C2 are compatible operation 290 may be carried out for pairing the first and second electronic components C1 and C2 of the electronic system 100. This was described/exemplified above with reference to FIG. 2D and is also further described in more detail below with reference to 4C.

Figure 4A:
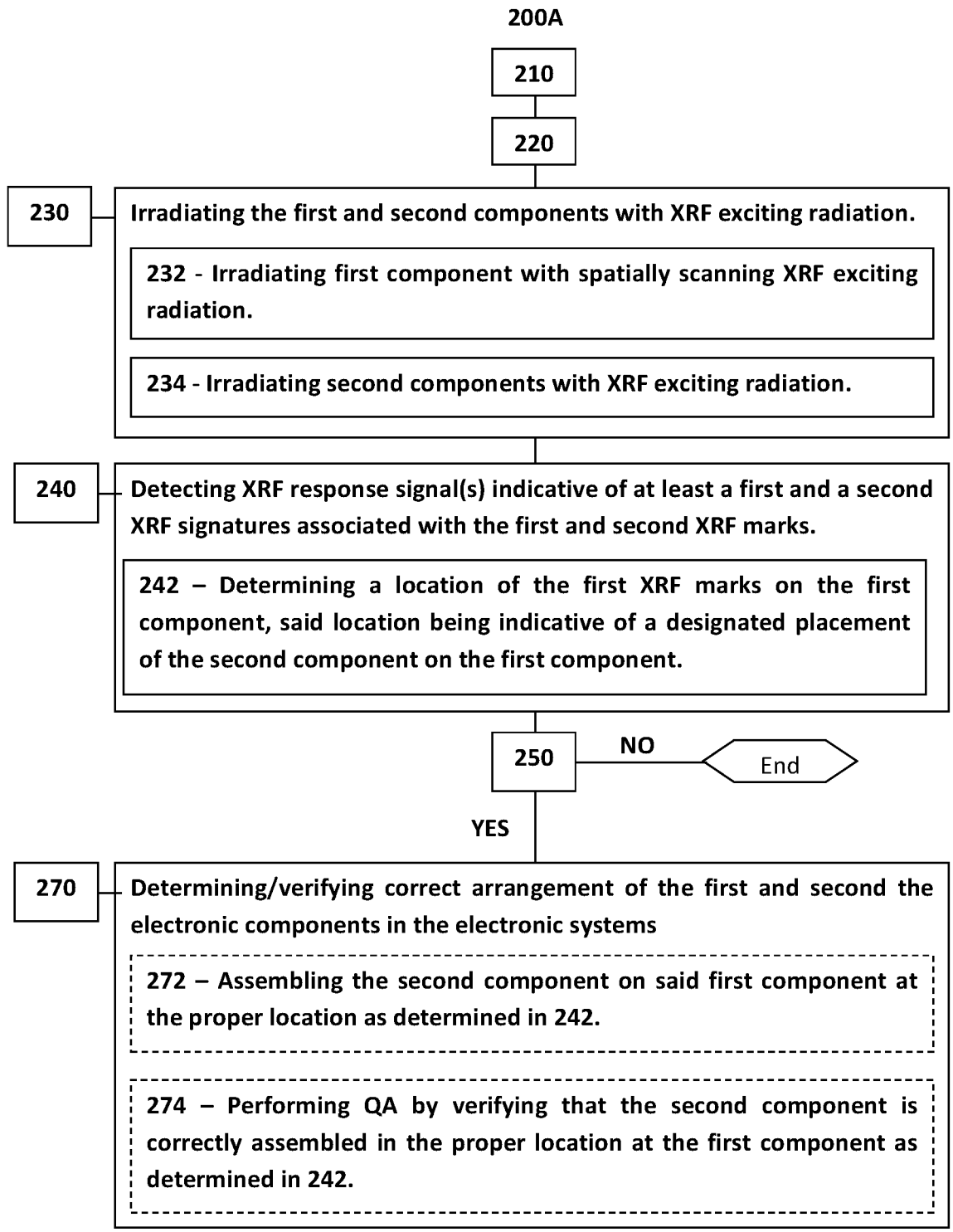
FIGS. 4A to 4C are flow chart of methods which may be carried out for verifying compatibility of components of an system according to various embodiments of the present invention.

Reference is now made to FIG. 4A which is a flow chart of a method 200A for verifying compatibility of components (e.g. C1 and C2) of an electronic system (e.g. 100) and determining/verifying corrected placement/arrangement of the components in the electronic system. Method 200A may be carried out for example in cases where the first component C1 is an electronic circuit board and the second component C2 is an electronic component associated with a designated place LC2 on the circuit board C1. It should be noted, that method 200A includes operations that are similar to those described above with reference to the method 200 of FIG. 3, which are marked by similar reference numerals in the flow chart 200A and are therefore not described in details in the following.

Operation 230 of method 200A includes irradiating, operations 232 and 234, of the first and second components C1 and C2 with XRF exciting radiation. In this example, one of the components, (e.g. the first component C1 being the circuit board,) may be irradiated operation 232 with spatially scanning XRF exciting radiation, to thereby determined the location (e.g. LC2 designated for the second component, or a location indicative of the location LC2) on the first component C1.

In this case the first XRF marking composition $XRFM_1$ is spatially located on the circuit board at the designated location LC2 of the second component (or a location indicative thereof) and therefore spatially located on said circuit board at said designated location of the second component on the circuit board.

In this embodiment, operation 240 for detecting XRF response signals from the components of the system includes the operation 242 for determining a location LC2 of the first XRF mark $XRFM_1$ on the first component C1 (PCB). This may be for example achieved by monitoring the state (position/angular orientation of the radiation beam) of the spatially scanning XRF exciting radiation from the scanning XRF analyzer, at the time the first XRF signature $XRFS_1$ (e.g. of a signature corresponding/matching the signature $XRFS_2$ from the second component C2) is identified and thereby determining the location LC2 of the first XRF mark $XRFM_1$ on the PCB. This location LC2 is thus indicative of a designated placement of the second component C2 on the PCB/first component C1.

Accordingly in this embodiment the method 200A further includes operation 270 which is carried out to determine the correct arrangement (and proper placement location LC2) of the second component C2 on the first component (circuit board) C1. Indeed identifying the designated location is based on a correspondence between the first signature obtained from the designated location LC2 and the second signature obtained from the second component. Optionally, method 200A includes operation 272 for assembling (e.g. automatically assembling) the second component C2 on the first component C1 at the proper placement location LC2. Optionally, alternatively or additionally, method 200A includes operation 274 for performing quality assurance (QA) by verifying that the second component is correctly assembled on said first component at the proper placement location. Indeed in this case the component C2 may already be mounted on the designated location LC2, and accordingly the XRF signatures $XRFS_1$ and $XRFS_2$ may be obtained together as in a cumulative/composite signature CXRFS including them both. This is described in more details with reference to FIG. 4B.

Figure 4B:
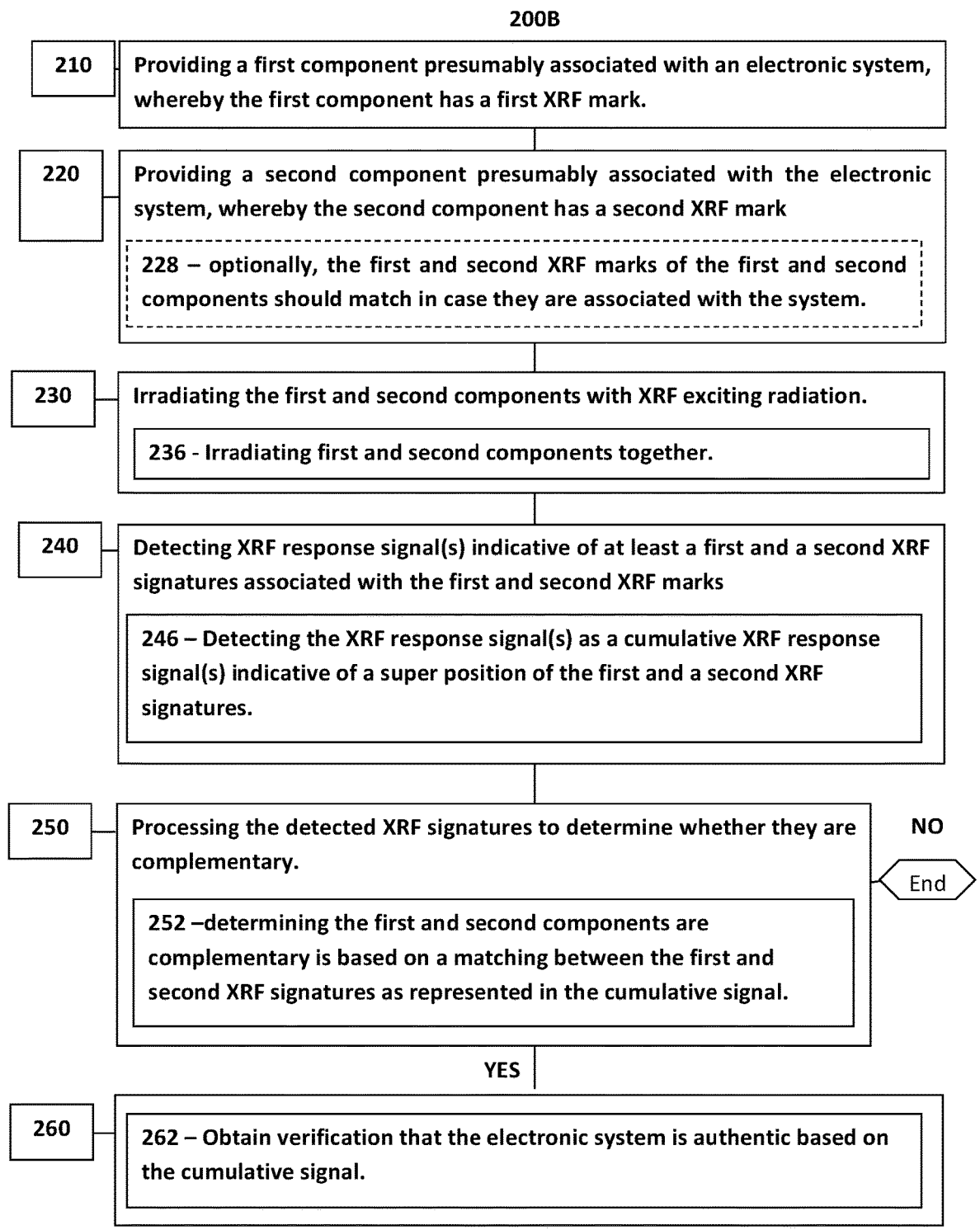

FIG. 4B is a flow chart 200B of a method according to an embodiment of the present invention for determining whether a two or more components C1 and C2 of an electronic system 100, which are located/connected together, are compatible with one another. It should be noted that generally the method 200B may be combined with the method 200A (which as described above utilizes the scanning XRF analyzer), for the purpose of carrying out QA and/or authenticity and/or counterfeit checks of assembled electronic systems. It should also be noted that where method 200B includes operations that are similar to those described above with reference to the method 200 of FIG. 3 and/or to the method of FIG. 4A, such operations are marked by similar reference numerals in the flow chart 200B and are not described in details in the following.

Thus in operations 210 and 220 of method 200B includes providing a first and a second components C1 and C2 presumably associated with the electronic system 100 and optionally assembled together, whereby the first component has a first XRF mark and the second component has a second XRF mark. Optionally (228 in the figure) the first and second XRF marks of the first and second components the first and second XRF marks should match in case the components C1 and C2 are complementary associated with the system 100, and should be also respectively configured for providing non-interfering XRF signals/signatures.

Operation 230 of method 200B for irradiating the first and second components with XRF exciting radiation includes operation 236 for irradiating the first and second components together with XRF exciting radiation. Operation 240 of method 200B for detecting XRF response signal(s) indicative of the XRF signatures of components C1 and C2, includes in method 200B detection of an composite XRF response signal indicative of a super position of the first and a second XRF signatures of the first and second components. Accordingly operation 250 in the method 200B for determining whether there is a match between the first and second XRF signatures, includes operation 252 for determining whether the first and second components are complementary is based on a matching between the first and second XRF signatures that are represented in the cumulative/composite XRF signature CXRFS (see for example row 2 in table 1 of FIG. 1).

This allows verifying if the components, C1 and C2, assembled together are complementary and thus allows to authenticate the electronic system based on the match between the first and second XRF signatures (as indicated in operation 262). In this regards the first component C1 may be an electronic component and the second component C2 may be a casing/packaging thereof. For example the first and second components may constitute parts of a chip assembly, as described above with reference to FIG. 2C.

Figure 4C:
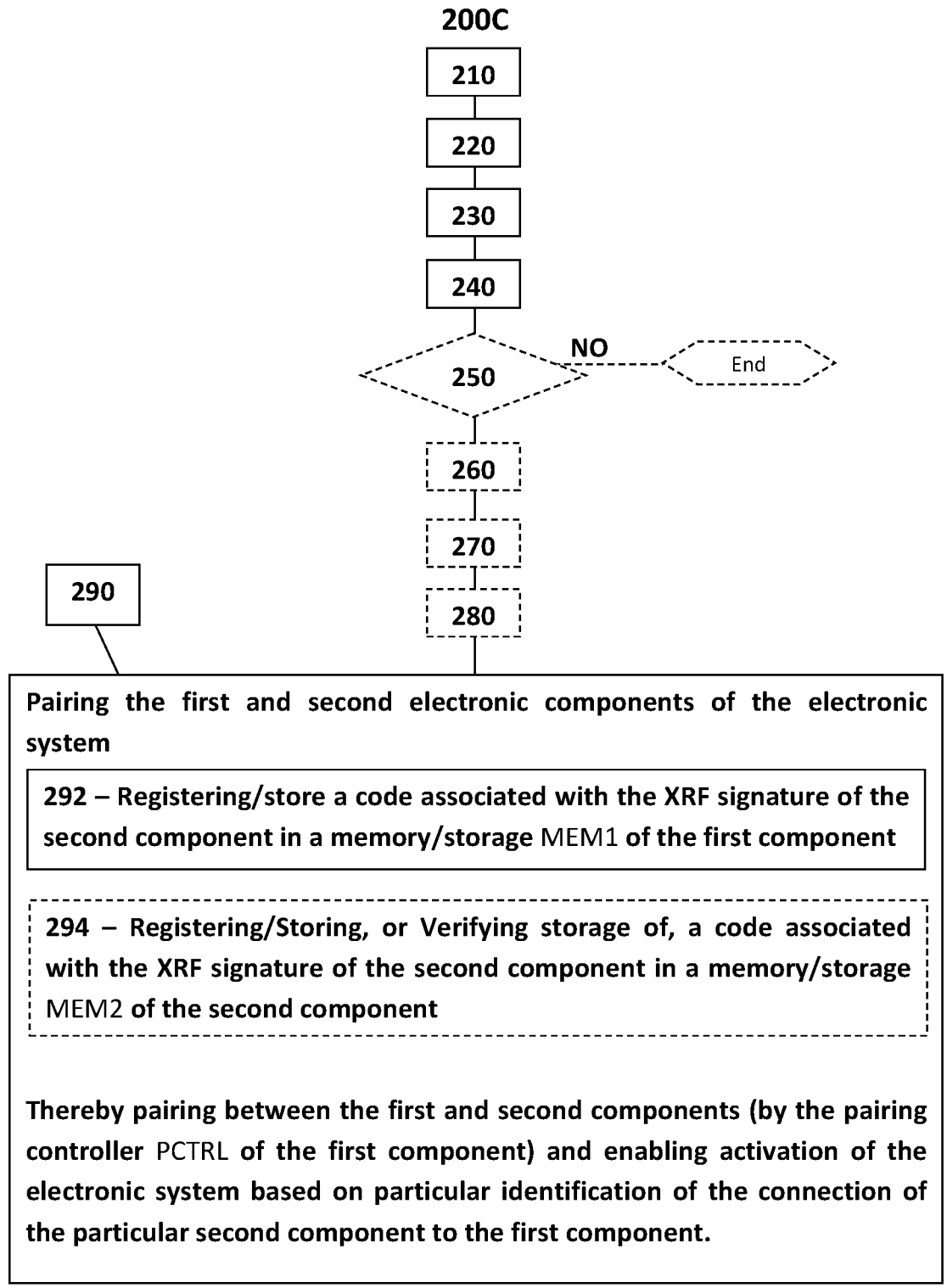

Reference is now made to FIG. 4C which shows a flow chart 200C of a method according to an embodiment of the present invention for pairing between two components of an electronic system (e.g. providing elemental pairing between the components), possibly only in case the components are compatible.

It should also be noted that where method 200C includes operations that are similar to those described above with reference to the method 200 of FIG. 3 and/or with reference to the methods of FIGS. 4A and 4B, such operations are marked by similar reference numerals in the flow chart 200C and are not described in details in the following. It is also noted that the non-essential/optional operations of this method 200C (e.g. operation 250 for verifying/determining whether the components C1 and C2) are compatible are marked in the figure with dashed lines.

Method 200C includes operation 290, which is carried out in addition to one or more of the above described operations 210 to 280 (some of which may be optional as illustrated in the figure). Operation 290 is carried out for pairing the first and second electronic components C1 and C2 of the electronic system 100, which may be two electronic devices of a distributed electronic system. Operation 290 includes operation 292 registering a code (a first data portion) associated with the XRF signature (e.g. $XRFS_2$) of a certain component (e.g. C2) of the electronic system 100 in a data storage module (e.g. memory MEM1) of another component (e.g. C1) of the system 100. Optionally, operation 290 also includes carrying out optional operation 294. This optional operation should be carried out for example case a code (e.g. a second data portion) corresponding to the XRF signature of that certain component C2 is not stored in a data storage module (memory MEM2) of that component C2 (e.g. generally such code (second data portion) may already be stored in the memory of the component C2 during its manufacture). Optional operation 294 includes registering the code (second data portion) corresponding to the XRF signature of that certain component C2 in the memory MEM2 of that certain component C2, or at least verifying that such code (second data portion) is indeed registered/stored in the memory MEM2.

Thus operation 290 enables enabling activation of the electronic system 100 based on particular identification that the specific components of the system are connected together (identifying that the connection between the certain component C2 and the another component C1).

Method 200C, and particularly operation 290 may be for example carried out for pairing to devices, C1 and C2 such as those illustrated in FIG. 2D above. In such examples the first component C1 is a first electronic device including a memory, for storing a first data portion (code) indicative of a correspondence between said first and second XRF signatures. The second component C2 is a second device comprising a second memory capable of storing a second data portion (e.g. the same code or a corresponding code) which is indicative of a correspondence between first and second XRF signatures. At least one of said first and second devices, C1 and C2, may include or be associated with a pairing/activation controller ACTRL that is configured and operable for obtaining the first and second data portions (codes) from the memories MEM1 and MEM2 and processing them to determine whether the first and second devices are paired to enable conditioned activation of mutual operation of the first and second devices based on a pairing between them.

As indicated above, in various embodiments of the present invention the XRF markings $XRFM_1$ and $XRFM_2$ may be applied to (e.g. applied on and/or embedded/blended) different substrate materials of different components of the electronic system 100, and accordingly different marking compositions of different components may be configured-with, or include, different promoters and/or different binder materials in accordance with the substrate to which they are to be applied. Indeed the different substrate materials and/or the different binder and/or promoters) used in different marking compositions may result with detection of different XRF background clutter, when measuring the XRF of different components of the system which are made from different substrates. Additionally, different textures and surface topologies (e.g. the surface of the substrate may be smooth or on the other hand may include recesses and/or protrusion) may also affect the measured XRF signals (for instance, due to variance in angles between the radiation source the surface of the substrate and the detector). The XRF signals measured by the detector will therefore other components in addition to the XRF signature which is determined by the different substrates. This difference in the clutter and other components might affect the XRF signature emanating from the object and the code word identified/determined thereby. In order to solve that a different calibration of the XRF analyzer may be used for different substrates and/or textures to which the XRF marking is applied so as to determine the respective XRF signatures of the marking compositions when applied to the different objects (different substrates and/or textures).

The present invention provides a novel calibration technique/method for calibrating XRF analyzers, in order to allow accurate measurements of XRF signatures (e.g. $XRFS_1$ and $XRFS_2$) of XRF marking compositions, which are embedded/located at different components (e.g. C1 and C2) of the system 100, possibly embedded located on different substrate materials of those components. This technique may be used in various implementations of the present invention to facilitate accurate detection and measurement of the XRF signatures $XRFS_1$ and $XRFS_2$ of the different components and to enable reliable comparison between them (e.g. using the predetermined condition and/or reference data as described above) to reliably determine whether the components are compatible. This calibration technique is described in the following with reference to FIG. 5A. Advantageously the calibration technique of FIG. 5A provides a simple way to determine the calibration data for marking new types of substrates without having to perform specific calibration to each new type substrate (e.g. having different material composition and/or different texture and/or marking application technique) which is to be marked by the XRF marking of the invention.

Figure 5A:
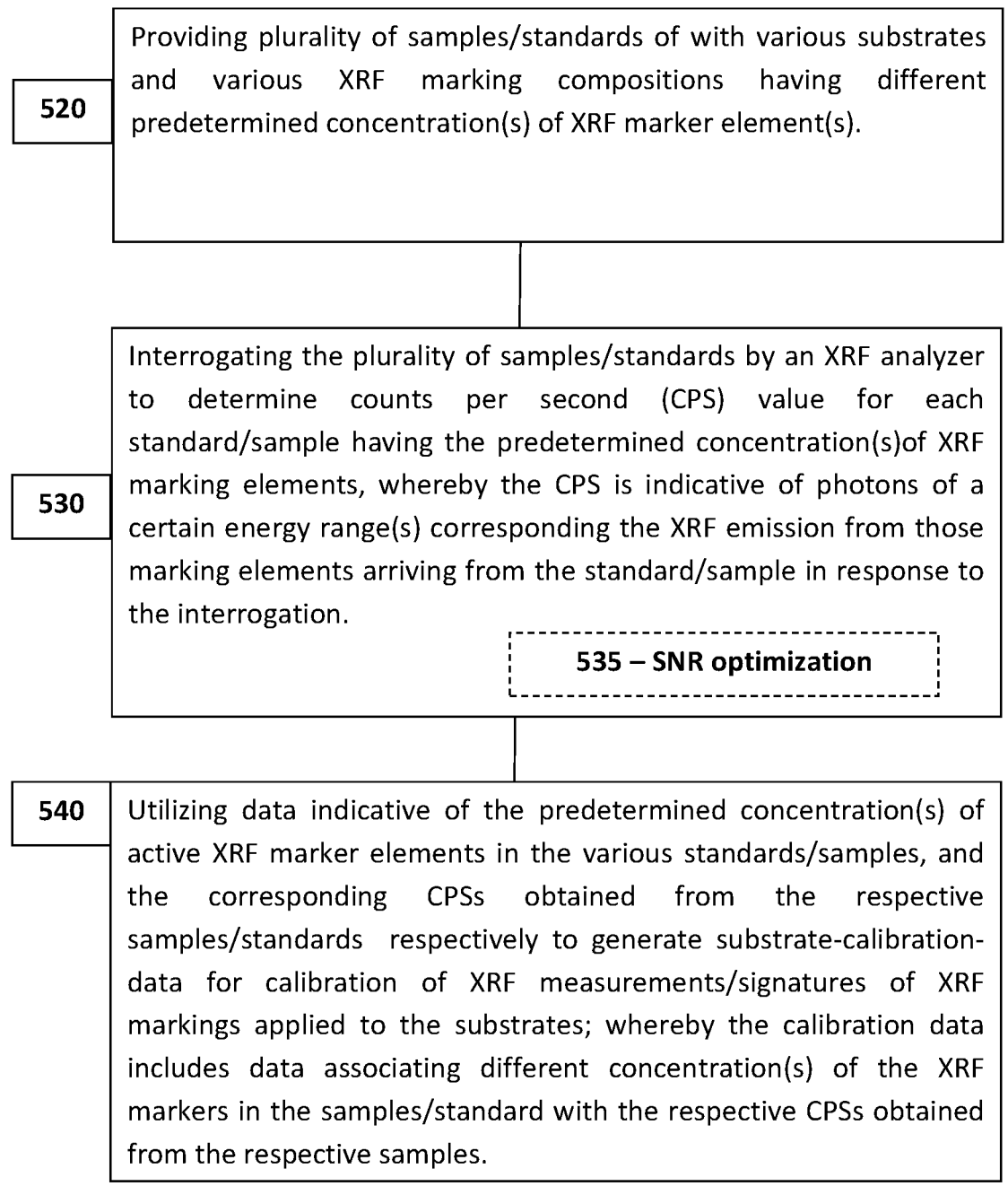
FIG. 5A is a flow chart of a calibration technique for use with XRF analyzer to enable accurate measurement of concentrations of XRF responsive marker materials in embedded/applied to various substrates.

Reference is made to FIG. 5A which is a flow chart of a method 500A for multi-substrate calibration of an XRF analyzer according to an embodiment of the present invention.

The method 500A provides for obtaining an optimal calibration of XRF analyzers, enabling the accurate identification of one or more XRF marking elements/materials, which may be deposited on various substrates (e.g. media) by various deposition methods as exemplified for example in Table 2 and/or in sections (a) to (i) above. In general the calibration method 500 provides for generating a calibration data (e.g. in the form of, or indicative of, a curve/plot) associating the counts collected in a time period (e.g. counts per second (CPS)) of x-ray photons within certain energy range(s) that are received from a component (e.g. C1) of the electronic system 100 with the concentration of a corresponding XRF marker element/material (which emits XRF in the same energy range(s)) that is included in the component (e.g. C1), and practically regardless of the substrate at which the XRF marker is deposited in the component. In other words, the method 500A provides for translating the CPS of one or more peak of an x-ray spectrum of XRF emission received from the component, into concentration (commonly measured in particles per million (ppm)) of the XRF marking element in that component, while being substantially indifferent to the substrate of the components on to which the XRF marking composition is applied and/or also regardless of the types of the additional materials (e.g. adhesives/binders/promoters) which are used in the XRF marking compositions for binding the XRF marking element(s) to the particular substrate of particular components, and the type of the substrate. This facilitates utilizing the technique of the present invention with various types of components of the electronic systems and embedding the XRF markers at different substrates.

Calibration method 500A is performed by utilizing a plurality of samples (also referred to herein as standards) in which one or more XRF marking element(s) is/are present in various known concentration(s) in a various media or substrates (where typically there are a number of samples with a number of concentrations for each substrate type). The standards/samples are then interrogated using the XRF analyzer. That is, the standards/samples are irradiated with x-ray or gamma-ray radiation and the secondary radiation arriving from the standards/samples in response are measured, thus receiving a CPS value for each of the samples/samples which are respectively associated with known concentration(s) of the XRF marking elements. Then reference calibration data for the calibrating XRF signals is based on the data acquired from the standard samples. The pair (CPS value, concentration) represents a point in the CPS Vs. concentration (PPM) plane and the calibration curve is generated by fitting a curve to the set of measured points (e.g. by the method of least squares which generates the 'best' linear curve). Commonly, the samples standards are made of known materials containing varying concentrations of the XRF marker element(s), and the calibration is intended to be used for finding concentrations of the XRF marker element in a media of the type used in the samples/standards (e.g. metals, polymers, fabric). Therefore calibration is performed while using each type of media/substrate which may include XRF markings in the components of interest. This is because each substrate generates different background x-ray radiation, therefore calibration (calibration curve) made with samples/standards of one group of substrates would generally not be suitable for measurements taken with other types of substrates). More specifically, method 500A includes performing the following operations 520 to 540 which are carried out for the plurality of various substrate (e.g. media) material on to which XRF markings are to be applied by various binding techniques:

Operation 520 includes providing plurality of samples/standards of a plurality of substrate materials whereby for each substrate there may be several samples with XRF marking compositions having different predetermined concentration(s) of XRF marker element(s).

Operation 530 includes interrogating the plurality of samples/standards by an XRF analyzer to determine counts per second (CPS) value for each standard/sample having the predetermined concentration(s) of XRF marking elements, whereby the CPS is indicative of photons of a certain energy range(s) corresponding the XRF emission from those marking elements arriving from the standard/sample in response to the interrogation; and Operation 540 includes utilizing data indicative of the predetermined concentration(s) (CNCTR) of active XRF marker elements in the various standards/samples (CNCTR), and the corresponding CPSs obtained from the respective samples/standards respectively to generate XRF-calibration-data for calibration of XRF measurements/signatures of XRF markings applied to various substrates. The XRF-calibration-data includes data associating different concentration(s) of the XRF markers in the samples/standard with the respective CPSs obtained therefrom. Accordingly, the XRF-calibration-data allows for calibration the spectral response of XRF signatures determine (represent those signatures) in terms of the concentrations of the XRF marking elements located at the substrate.

Thus, according to various embodiments of the present invention an XRF reader system that is configured for carrying out XRF measurements of XRF markings on different substrates, may be equipped with the calibration data as obtained by method 500A above and may be configured to utilize the calibration data to convert/translate the XRF signatures obtained from XRF markings on different substrates to a common basis (e.g. being the marking material concentration bases instead of the spectral basis at which the signatures are initially obtained from the XRF analyzer). Accordingly, this allows accurate and reliable processing and/or comparison XRF markings applied to different components made with different substrates (e.g. comparison of between the XRF markings of the components and/or between them and a reference data.

It should be noted that optionally according to some embodiments of the present invention, operation 530 which is carried out for interrogating the plurality of samples/standards by an XRF analyzer, includes an SNR optimization step 535 which is carried out to optimize/determine the parameters of the XRF exciting radiation which should be emitted during the XRF interrogation in order to optimize the SNR of the XRF signatures read from the standards/samples. SNR optimization step 535 may for example include the following:

(I) Applying XRF measurements to the plurality of samples for measuring the XRF spectrum arriving from each sample (spectrum of secondary x-ray radiation arriving from each sample in response to x-ray or gamma-ray radiation).

(II) Processing the XRF spectrum arriving from each sample to determine an XRF signature of the sample/standard—(by identifying the peak (or peaks) associated with the XRF marker elements for each spectrum).
(III) Evaluating the signal to noise ratios (SNR) of the XRF signatures of the samples/standards and selecting from the samples/standards, a sample/standard having medium ('average') SNR. E.g. selecting a sample/standard whose SNR is closest to the average SNR of all the standards, and/or alternatively, randomly choosing a standard, whose SNR is not too close (closer than a preselected distance) to one of the extreme values (best or worst)).
(IV) Varying the XRF measurement parameters (e.g. XRF tube voltage, XRF tube current, XRF filter, and distance from the standard) to optimizing the SNR of the XRF signature from the selected standard/sample.
(V) Then, carrying the operation 530 as described above for interrogating/measuring the XRF spectrum (signatures) of all of the standards/samples of all substrates but with the selected/optimized XRF measurement parameters.
(VI) Optionally, discarding spectrum measurements of standards whose SNR is lower than a preselected value.
After performing the operation 530 in the way to optimize the SNR, the method further continues to operation 540 for obtaining a calibration data/curve.
Thus, the calibration data for the different substrates, as obtained in operation 540 indicates a fit between the XRF signatures measured in terms of CPS vs. wavelengths/energy ($\lambda$) to the XRF signatures in terms of the concentrations of the XRF marking elements in different substrates, as illustrated in Table 3 above. Optionally the calibration data may also include data indicative of the XRF measurement parameters (e.g. XRF tube voltage, XRF tube current, XRF filter, and distance from the standard) which are obtained in operation 535 and which should be used for measuring the XRF responses from different substrates.

Figure 5B:
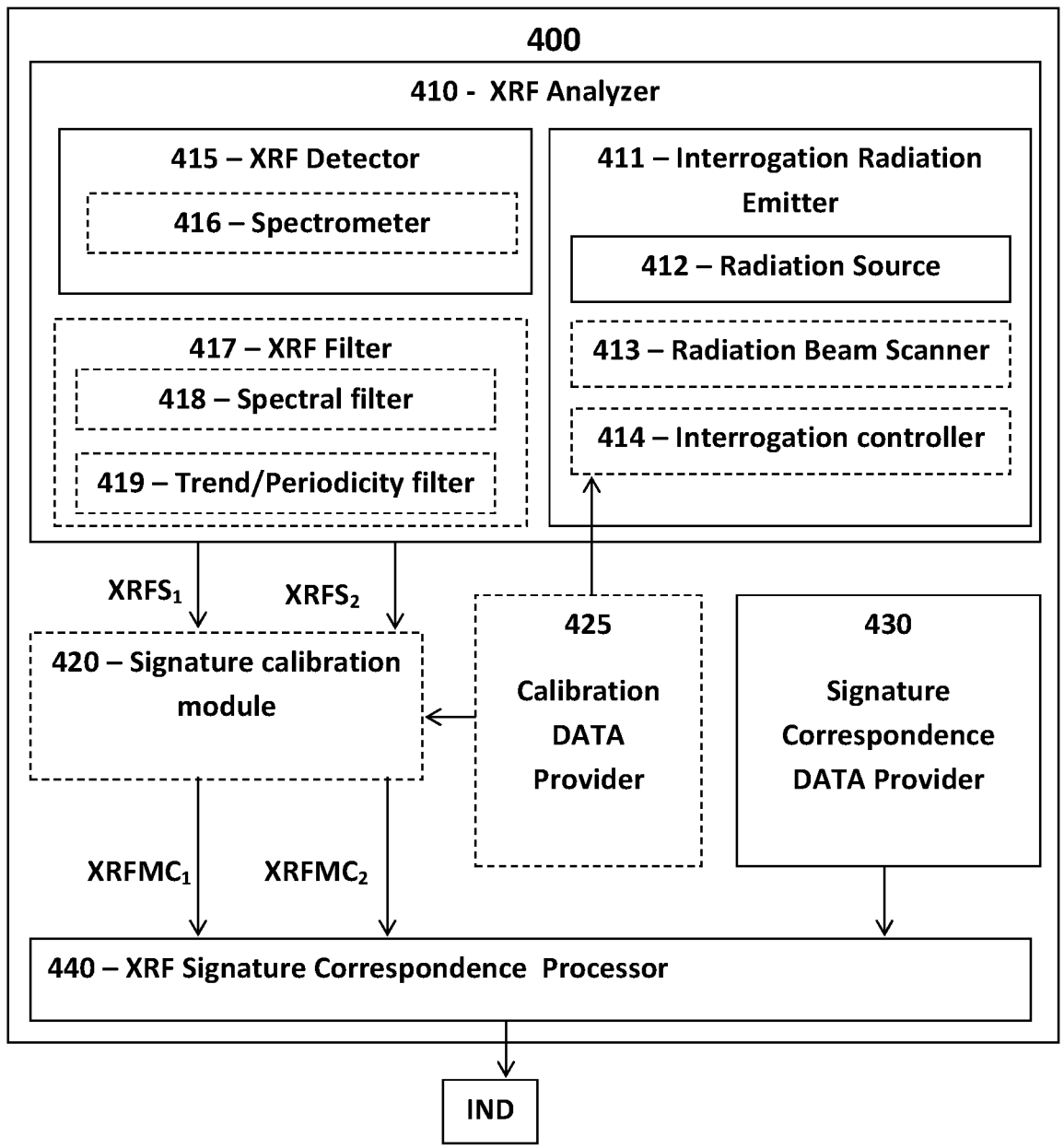
FIG. 5B is a block diagram of an XRF verification reader configured according to an embodiment of the present invention for verifying compatibility of electron components of an electronic system.

Reference is now made to FIG. 5B which is a block diagram of an XRF verification reader 400 for use for verification of compatibility of components of electronic system according to an embodiment of the present invention.

The XRF verification reader 400 includes an XRF analyzer 410 adapted for performing XRF measurements on different components (e.g. C1 and C2) of electronic systems (e.g. 100), and providing data indicative of XRF signatures $XRFS_1$ and $XRFS_2$ obtained from XRF markings thereon. The XRF verification reader 400 also includes a XRF signature correspondence data provider 430 and XRF signature correspondence processor 440 which may be used together to determine whether the XRF signatures $XRFS_1$ and $XRFS_2$ obtained from the XRF analyzer 410 correspond to one another, and in that case issue indication that IND that the components (e.g. C1 and C2) which XRF markings are measured by the XRF analyzer 410 are compatible or otherwise issue indication IND that the components are not compatible.

In certain embodiments the XRF signature correspondence data provider 430 includes a data storage facility (e.g. memory) that stores data, such as a predetermined condition data indicative of a predetermined condition according to which a match between different XRF signatures, $XRFS_1$ and $XRFS_2$, should be determined, and and/or storing reference data, such as a LUT that associates corresponding XRF signatures. Alternatively or additionally, in certain embodiments the XRF signature correspondence data provider 430 includes communication utility adapted for communicating, e.g. with a remote data source, to obtain the reference data indicative of the correspondence between the XRF signatures.

Accordingly, the XRF signature correspondence processor 440 may be connected, directly or in directly to the XRF analyzer 410 for receiving therefrom data indicative of the XRF signatures, $XRFS_1$ and $XRFS_2$, and may also be connected to the signature correspondence data provider 430 for receiving data/condition indicative of correspondence/matching between the signatures. The XRF signature correspondence processor 430 processes the XRF signatures, $XRFS_1$ and $XRFS_2$ based on the correspondence data and determines whether they corresponds, according to any one of the techniques described above.

The XRF analyzer 410 generally include an interrogation radiation emitter 411 which includes an X-Ray and/or Gamma-ray radiation source 412 for emitting interrogation radiation towards an inspected object/component, and an XRF detector 415, possibly comprising a spectrometer 416, adapted for detecting the XRF radiation response from the interrogated object and possibly obtaining data indicative of its spectral composition.

The XRF analyzer 410 may also include one or more filters 417 for filtering the detected XRF response. These may include a spectral filter 418 for filtering out les relevant spectral components form the response, leaving in the detected XRF signatures only the spectral regions at which an XRF response of interest is expected from the interrogated object/component. Also the filters 417 may include a trend and/or periodicity filter 419 (such as that described for example in PCT patent application No. PCT/IL2016/050340 which is incorporated herein by reference), which is operable for enhancing the SNR of the XRF signals/signatures by removing the trend and/or the periodic spectral components therefrom.

In some embodiments the interrogation radiation emitter 411 includes a radiation beam scanner 413 which is configured and operable for spatially directing and/or focusing the interrogation radiation beam outputted from the radiation source 412 so as to scan an interrogated object (e.g. electronic system 100) with the beam, and thereby provide data indicative of the locations (e.g. LC1 and LC2 in FIG. 2B) at which various components of the system may be assembled.

Optionally, in some embodiments the XRF verification reader 400 also includes an XRF signature calibration module 420 and a calibration DATA Provider 425 which are operable together to calibrate the XRF signatures, $XRFS_1$ and $XRFS_2$ which may be obtained from XRF markings which are embedded/applied to different components made/including different substrate materials. The calibration DATA Provider 425 may be for example a storage facility/memory for XRF calibration data for different substrates. The calibration data may for example similar to that obtained by method 500A above and may include curve fitting (e.g. curve fitting) data indicative of a substrate specific relationship between the spectral curves (obtained as a function of CPS vs. wavelength/energy) in the XRF signatures $XRFS_1$ and $XRFS_2$ and the concentration of XRF marking elements in the XRF marking compositions marking the substrates of the components C1 and C2 from which the XRF signatures $XRFS_1$ and $XRFS_2$ were obtained. Accordingly the XRF signature calibration module 420 may utilize the calibration data to convert the $XRFS_1$ and $XRFS_2$ from the spectral basis to respective XRF signatures, $XRFMC_1$ and $XRFMC_2$, represented in the basis of the concentrations of the XRF markers in the marking compositions used to mark the respective substrates from which the XRF signatures were obtained. This allows comparing XRF markings of different components and/or form different substrates.

Optionally the calibration data from the calibration DATA Provider 425 also includes the data indicative of the XRF measurement parameters (e.g. XRF tube voltage, XRF tube current, XRF filter, and distance from the standard) as obtained in operation 535 described above, Accordingly the interrogation radiation emitter 411 may optionally include an Interrogation controller 414 configured and operable for receiving the reference data about the XRF measurement parameters corresponding to the substrate(s) of the component(s) on which XRF interrogation is to be applied, and adjusting the emission properties of the radiation emitter accordingly, thereby calibration the radiation emission of the interrogated components at which the XRF marking resides.

It should be understood both the XRF signature calibration module 420 and a calibration DATA Provider 425 are optional and may be obviated. For example, as discussed above in some cases in the code word of an XRF signature is not indicative of the concentrations of the XRF marking elements in the marking composition but is associated with XRF signature that is read from the marked object/component as a whole, including the marking composition as well as the effects of the substrate of the component to which the marking composition is applied and the method of application of the marking. In that case there may be not need to determine the concentrations of the marker elements but instead the XRF signature from the component itself may represent the code-word of the marking. Accordingly in this case calibration module may be obviated, while possibly relaying on the XRF signature correspondence data provider 430 and XRF signature correspondence processor 440 to determine whether the XRF signatures $XRFS_1$ and $XRFS_2$ (which may be obtained from the same marking composition applied to different components/substrates) correspond to one another.

The invention claimed is:

1. An electronic system comprising:
    a plurality of components comprising at least a first and a second electronic components, wherein:
        the first electronic component includes a first XRF marking composition configured for emitting a first XRF signal having a first XRF signature in response to irradiation thereof by XRF exciting radiation;
        the second electronic component includes a second XRF marking composition configured for emitting a second XRF signal having a second XRF signature in response to irradiation thereof by XRF exciting radiation; and
        wherein said first and second XRF markings are respectively configured such that the first XRF signature of the first electronic component corresponds to the second XRF signature of the second electronic component thereby enabling verification that said first and second electronic components are respectively compatible components of said electronic system.

2. The electronic system of claim 1 wherein a correspondence between said first and second XRF signatures is based on a predetermined mutual relationship condition between the signatures, thereby enabling in situ verification that the first and second components are complementary while obviating a need for using reference data.

3. The electronic system of claim 1 wherein a correspondence between said first and second XRF signatures is determined based on a reference data associating signatures of complementary components.

4. The electronic system of claim 1 wherein the first component is an electronic circuit board and the second component is an electronic component associated with a designated place on the circuit board.

5. The electronic system of claim 4 wherein:
    (I) the first marking composition is embedded in the circuit board in one or more of the following:
        (a) the first marking composition may be blended with polymers comprising a solder mask applied to the circuit board during its fabrication;
        (b) the first marking composition is blended with ink of prints printed on the circuit board;
        (c) the first marking composition is blended with the compounds comprising under-fill binding of one or more components to the circuit board;
        (d) the first marking composition may be blended with polymers of the packaging of some of the components on the circuit board;
        (e) the marking composition is embedded in an overly or coating of the solder mask or of components of the circuit board;
        (f) the marking composition is blended with polymers applied to through vertical interconnect access (VIA) holes on the circuit board;
        (g) the marking composition is contained in a special 'fake' component designed for carrying the marking composition; and
    (II) the second component is an electronic component mountable on the circuit board and said second marking composition is embedded in said electronic component in one or more of the following:
        (h) the second marking composition is blended with ink of prints printed on the electronic component;
        (i) the second marking composition may be blended with polymers of the packaging of the second component;
        (j) the marking composition is blended with polymers applied to through vertical interconnect access (VIA) holes of the second component.

6. The electronic system of claim 4 wherein the first XRF marking is spatially located on said circuit board at said designated location of the second component on the circuit board, thereby enabling to utilize a spatially focused XRF reader to identify said designated location based on a correspondence between said first and second signatures and thereby verify proper placement of said second component on the circuit board.

7. The electronic system of claim 1, wherein the first component is an electronic component and the second component is a casing packaging said electronic component.

8. The electronic system of claim 7, wherein said first and second XRF marking compositions are configured such that in response to irradiation of the system by an XRF exciting radiation, they emit together a composite XRF signal comprising said first and second XRF signals indicative of said first and second XRF signatures, and such that the first and second XRF signatures do not interfere with one another in the composite XRF signal thereby enabling verification that said first and second electronic components by irradiating said system with the XRF exciting radiation, enabling to obviate a need to open said casing.

9. The electronic system of claim 1 wherein:
    the first component is a first device comprising a first data storage module capable of storing a first data portion indicative of a correspondence between said first and second XRF signatures;

the second component is a second device comprising a second data storage module capable of storing a second data portion indicative of a correspondence between said first and second XRF signatures; and wherein at least one of said first and second devices comprises a pairing controller configured and operable for: (i) accessing said first and second data storage modules upon wired or wireless connation between said first and second devices, (ii) retrieving said first and second data portions from said first and second data storage modules respectively, (iii) processing said first and second data portions to determine whether said first device is paired with said second device based a correspondence between the first and second XRF signatures of said first and second devices; and (iv) enabling conditioned activation of mutual operation of said first and second devices based on a pairing between said first and second devices.

10. The electronic system of claim 9 wherein at least one of said first and second devices is a smart wearable device; and wherein the XRF marking composition is included in said smart wearable device in at least one of the following:

the smart wearable device includes a fabric comprising natural fibers and wherein said second XRF marking compositions comprises Mordants used for dying said natural fibers; and the smart wearable device includes a fabric comprising synthetic fibers and wherein said second XRF marking compositions is introduced into said synthetic fibers during an extrusion process thereof.

11. The electronic system of claim 9 wherein said electronic system is a healthcare system and wherein at least one of said first and second devices is configured for monitoring one or more conditions of a user, and at least one of said first and second devices is configured and operable for providing treatment to said user based on the monitored condition.

12. A method for verifying compatibility of components of an electronic system comprising at least a first and a second electronic components, the method comprising:

providing a first component and a second components presumably associated with the electronic system;

irradiating the first and second components with XRF exciting radiation;

detecting one or more XRF response signals emitted in response to said irradiating from the first and second components;

processing the one or more XRF response signals to identify a first and a second XRF signatures associated respectively with first and second XRF marking compositions on said first and second components;

upon identification of the of the first and second XRF signatures, processing said first and second signatures to determine a correspondence between them, and verifying a verifying compatibility of said first and second components to the electronic system based on said correspondence.

13. The method of claim 12 wherein processing said first and second signatures to determine said correspondence between them comprises providing a certain predetermined condition indicative of a predetermined mutual relationship between complementary XRF signatures, and determining whether said first and second XRF signatures satisfy said predetermined condition thereby enabling in situ verification that the first and second components are compatible while obviating a need for using reference data.

14. The method of claim 12 wherein the first component is an electronic circuit board and the second component is an electronic component associated with a designated place on the circuit board, and said first XRF marking composition is spatially located on at said designated location; and wherein the method comprising determining correct arrangement of the second component on said circuit board by utilizing a scanning XRF reader to spatially scan said circuit board and identifying said designated location based on a correspondence between said first signature obtained from the designated location and said second signature, and thereby verifying proper placement location of said second component on the circuit board.

15. The method of claim 14 further comprising:
assembling the second component on said first component at said proper placement location; and, optionally,
performing quality assurance (QA) by verifying that the second component is correctly assembled on said first component at said proper placement location.

16. The method of claim 12 wherein the first and second components are connected together and wherein the method comprises:
(a) irradiating the first and second components together with XRF exciting radiation;
(b) detecting an XRF response signal as a composite XRF response signal indicative of a superposition of the first and a second XRF signatures of the first and second components; and
(c) determining whether there is a match between the first and second XRF signatures represented in the composite signal and thereby verifying that the first and second components are compatible and complementary components.

17. The method of claim 16, wherein said first and second XRF marking compositions are configured such that in response to irradiation of the system XRF exciting radiation they emit said composite XRF signal together whereby said composite XRF signal comprises said first and second XRF signals indicative of said first and second XRF signatures, such that the first and second XRF signatures do not interfere with one another in the composite XRF signal thereby enabling authenticating said electronic system by irradiating said system with said XRF exciting radiation, while obviating a need to open said casing.

18. The method of claim 12 comprising pairing the first and second electronic components of the electronic system; said pairing comprises:
registering a code associated with the XRF signature of a certain component of said first and second components in a data storage module of another component of said first and second component; and
at least in case said code is not stored in a data storage module of said certain component, registering said code in a data storage module of said certain component;
thereby enabling activation of the electronic system based on particular identification of the connection of the certain component and said another component.

19. The method of claim 18 wherein the first component is a first device comprising a first data storage module capable of storing a first data portion indicative of a correspondence between said first and second XRF signatures; wherein the second component is a second device comprising a second data storage module capable of storing a second data portion indicative of said correspondence between said first and second XRF signatures; and wherein at least one of said first and second devices comprises a pairing controller configured and operable for: (i) accessing said first and second data storage modules via wired or wireless connection between said first and second devices; (ii) retrieving said first and second data portions from said first and second data storage modules respectively; (iii) processing said first and second data portions to determine whether said first device is paired with said second device based on said correspondence between the first and second XRF signatures of said first and second devices; and (iv) enabling conditioned activation of mutual operation of said first and second devices based on the pairing between said first and second devices.

20. The electronic system of claim 18 wherein said first and second electronic components are components of a healthcare electronic system and whereby at least one of said first and second devices is configured for monitoring one or more conditions of a user, and at least one of said first and second electronic components is configured and operable for providing treatment to said user based on the monitored condition; and wherein providing said treatment is conditioned by that said pairing of the first and second devices electronic components.

21. A method for calibrating XRF measurements of XRF markings applied to one or more substrate materials comprising carrying out the following per each particular substrate material:
   providing plurality of samples of the various substrate materials and various XRF marking compositions having various predetermined concentrations of XRF marker elements;
   interrogating the plurality of samples by an XRF analyzer to determine for each sample a counts per second (CPS) value indicative of photons of a certain energy range(s) associated with the XRF marking elements;
   determining and storing calibration data XRF for use on measurements of XRF markers applied to said substrates, whereby said calibration data includes data associating the predetermined concentration of the XRF marker elements in the plurality of samples with the corresponding CPSs obtained from the samples.

* * * * *